United States Patent [19]
Gemert et al.

[11] Patent Number: 6,113,814
[45] Date of Patent: Sep. 5, 2000

[54] POLYMERIZABLE POLYALKOXYLATED NAPHTHOPYRANS

[75] Inventors: Barry Van Gemert, Murrysville; Anu Chopra, Monroeville; Anil Kumar, Pittsburgh, all of Pa.

[73] Assignee: Transitions Optical, Inc., Pinellas Park, Fla.

[21] Appl. No.: 09/437,982

[22] Filed: Nov. 10, 1999

Related U.S. Application Data

[63] Continuation-in-part of application No. 09/151,911, Sep. 11, 1998, abandoned.
[51] Int. Cl.$^7$ .......................... G02B 5/23; C07D 311/92; G02C 7/10
[52] U.S. Cl. .................... 252/586; 549/389; 549/331; 549/362; 549/382; 549/58; 549/60; 546/256; 546/280.4; 546/281.1; 546/282.7; 546/277.4; 546/282.4; 548/454; 524/110; 525/279; 525/403; 351/163
[58] Field of Search ............................ 252/586; 549/389, 549/331, 362, 382, 58, 60; 546/256, 280.4, 281.1, 282.7, 277.4, 282.4; 548/454; 524/110; 525/279, 403; 351/163

[56] References Cited

U.S. PATENT DOCUMENTS

| | | | |
|---|---|---|---|
| 4,719,296 | 1/1988 | Irie et al. .................... | 544/71 |
| 5,166,345 | 11/1992 | Akashi et al. ............... | 544/71 |
| 5,236,958 | 8/1993 | Miyashita .................. | 518/121 |
| 5,252,742 | 10/1993 | Miyashita .................. | 548/121 |
| 5,274,132 | 12/1993 | Van Gemert ............... | 252/586 |
| 5,359,085 | 10/1994 | Iwamoto et al. ........... | 548/468 |
| 5,458,814 | 10/1995 | Kumar et al. .............. | 252/586 |
| 5,466,398 | 11/1995 | Van Gemert et al. ....... | 252/586 |
| 5,488,119 | 1/1996 | Fischer-Reimann et al. ... | 552/201 |
| 5,520,853 | 5/1996 | Rickwood et al. .......... | 252/586 |
| 5,552,091 | 9/1996 | Kumar ....................... | 252/586 |
| 5,568,501 | 10/1996 | Kumar et al. .............. | 252/586 |
| 5,573,712 | 11/1996 | Kumar et al. .............. | 252/586 |
| 5,578,252 | 11/1996 | Van Gemert et al. ....... | 252/586 |
| 5,585,042 | 12/1996 | Knowles .................... | 252/586 |
| 5,637,262 | 6/1997 | Van Gemert et al. ....... | 252/586 |
| 5,645,767 | 7/1997 | Van Gemert ............... | 252/586 |
| 5,658,500 | 8/1997 | Kumar et al. .............. | 252/586 |
| 5,658,501 | 8/1997 | Kumar et al. .............. | 252/586 |
| 5,744,070 | 4/1998 | Kumar ....................... | 252/586 |
| 5,753,146 | 5/1998 | Van Gemert et al. ....... | 252/586 |

FOREIGN PATENT DOCUMENTS

| | | |
|---|---|---|
| 875509A1 | 11/1998 | European Pat. Off. . |
| 199 02 771A1 | 12/1999 | Germany . |
| 3-100091 | 4/1991 | Japan . |
| 3-91578 | 4/1991 | Japan . |
| WO 96/01884 | 1/1996 | WIPO . |
| WO97/05213 | 2/1997 | WIPO . |
| WO 98/04937 | 2/1998 | WIPO . |

OTHER PUBLICATIONS

Derwent Abstract, JP 5098252, Apr. 20, 1993.
Derwent Abstract, JP 8176139, Jul. 9, 1996.
Bradshaw, J.S., et al., "Synthesis of Macrocyclic Acetals Containing Lipophilic Substituents", Tetrahedron, vol. 43, No. 19, pp. 4271–4276, 1987.
Organic Synthesis, vol. 31, pp. 90–92, John Wiley & Sons, Inc., New York, 1951.
Ullmann's Encyclopedia of Industrial Chemistry, "Polymerization Processes", vol. A21, Fifth, Completely Revised Edition, pp. 305–306, 1992.

*Primary Examiner*—Philip Tucker
*Attorney, Agent, or Firm*—Frank P. Mallak; Irwin M. Stein

[57] ABSTRACT

Described are novel photochromic polymerizable polyalkoxylated naphthopyran compounds, examples of which are certain 2H-naphtho[1,2-b]pyrans, 3H-naphtho[2,1-b]pyrans and indeno[2,1-f]naphtho[1,2-b]pyrans each having at least one polyalkoxylated substituent of from 1 to 50 alkoxy units per substituent which is end-capped with a polymerizable group. Specific substituents are also present on the naphtho, indeno and pyrano portions of the compounds. These compounds may be represented by the following graphic formulae:

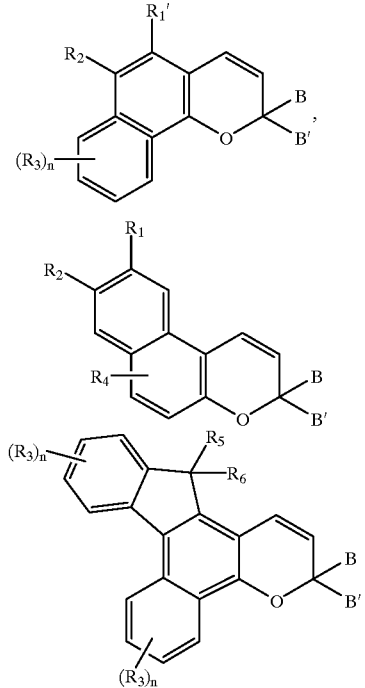

Also described are various substrates, e.g., paper, glass, polymeric organic materials, etc., that contain or that are coated with such compounds. Optically clear articles such as contact lenses or other plastic transparencies that incorporate the novel naphthopyran compounds or combinations thereof with complementary photochromic compounds, e.g., certain other naphthopyrans, indenonaphthopyrans, benzopyrans, oxazine-type compounds, etc., are also described.

21 Claims, No Drawings

POLYMERIZABLE POLYALKOXYLATED NAPHTHOPYRANS

CROSS REFERENCE TO RELATED APPLICATIONS

This application is a continuation-in-part of application Ser. No. 09/151,911 filed Sep. 11, 1998 now abandoned.

DESCRIPTION OF THE INVENTION

The present invention relates to certain novel naphthopyran compounds. More particularly, this invention relates to photochromic polymerizable polyalkoxylated naphthopyran compounds and to compositions and articles containing such novel photochromic compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. U.S. Pat. No. 5,458,814 describes photochromic 2,2-di-substituted-5,6-substituted-2H-naphtho[1,2-b]pyran compounds primarily for use in lenses and other plastic transparencies. These compounds have an acceptable fade rate in addition to a high activated intensity and a high coloration rate. U.S. Pat. No. 5,585,042 discloses 3,3-di-substituted-8-substituted-3H-naphtho[2,1-b]pyran compounds for similar uses. These compounds exhibit an improved solar response, a higher activating wavelength than unsubstituted naphthopyrans, and an acceptable bleach or fade rate. U.S. Pat. No. 5,645,767 describes photochromic indeno[2,1-f]naphtho[1,2-b]pyrans having a high activated intensity, an acceptable fade rate and high coloration rate.

International Patent Application WO 97/05213 describes a photochromic monomer having a photochromic dye moiety bonded to an organic spacer group which terminates with a polymerizable group. It is reported that when the photochromic monomer is incorporated into a cross-linking polymerizable casting composition, the photochromic material has a reduced sensitivity to temperature.

Although 3H-naphtho[2,1-b]pyrans, 2H-naphtho[1,2-b]pyrans and indeno[2,1-f]naphtho[1,2-b]pyrans of good intensity and reasonable fade are currently available, it is desirable to modify certain properties of the photochromic compound, such as the fade and/or activation rate, saturated optical density, sensitivity to elevated temperatures, fatigue rate and/or the formation of residual color, without changing its activated color. Modifications to such properties may be done to match the same properties of complementary photochromic compounds or to enable the use of such compounds in coatings, thin films or in rigid plastic matrices wherein the activation/fade kinetics of photochromic compounds are frequently slowed.

In accordance with the present invention, there have been discovered novel photochromic compounds; namely, certain 2H-naphtho[1,2-b]pyrans, 3H-naphtho[2,1-b]pyrans and indeno[2,1-f]naphtho[1,2-b]pyrans, that have at least one polyalkoxylated substituent terminated with a polymerizable group. Appropriate selection of the polyalkoxylated group, e.g., chain length and the number and nature of the alkoxy groups, and the polymerizable group enables modification of the aforementioned properties. Incorporation of a polymerizable group in the photochromic compound enables homopolymerization or co-polymerization of the compound with appropriate polymerizable compounds, and can reduce or prevent leaching of the photochromic compound from the polymer matrix into which it is incorporated. Depending on the location of the polymerizable polyalkoxylated substituent, certain other substituents may also be present on the naphtho, pyrano and indeno portions of the aforedescribed compounds.

DETAILED DESCRIPTION OF THE INVENTION

In accordance with the present invention, it has been discovered that certain properties, e.g., fade rate, activation rate, saturated optical density, fatigue rate, sensitivity to temperature, i.e., temperature dependency, and the formation of residual color in polymerizates, of selected photochromic 2H-naphtho[1,2-b]pyrans, 3H-naphtho[2,1-b]pyrans and indeno[2,1-f]naphtho[1,2-b]pyrans may be modified by including at least one polymerizable polyalkoxylated substituent on such compounds. The polymerizable polyalkoxylated substituent may have from 1 to 50 alkoxy units and may be located on the naphtho or indeno portion and/or on the pyrano portion of the naphthopyran or indenonaphthopyran.

The naphthopyrans of the present invention also may have certain other substituents. Specifically, the 2H-naphthopyrans may have substituents at the 5 and 6 positions and may have additional substituents at the 7, 8, 9 and 10 positions; the 3H naphthopyrans may have substituents at the 8 and 9 positions and may have additional substituents at the 5 and 6 positions; and the indeno-fused naphthopyrans may have certain substituents at the 5, 6, 7, 8, 9, 10, 11, 12 or 13 positions. The aforedescribed naphthopyrans may be represented by graphic formulae I, II and III in which the internal numbers 1 through 13 identify the ring atoms of the naphthopyrans and letters a through n represent the sides of the naphthopyran rings. In the definition of the substituents shown in the following graphic formulae I, II and III, like symbols have the same meaning unless stated otherwise.

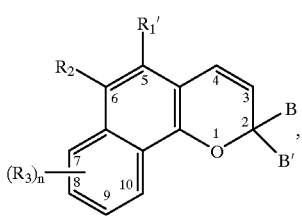

I

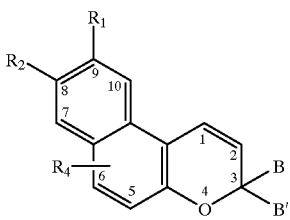

II or

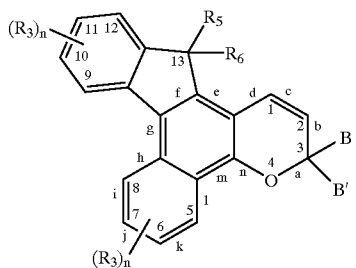

III

In graphic formulae I, II and III, $R_1$, $R_1'$, each $R_3$, $R_4$, $R_5$ or $R_6$ is the group R; $R_2$ is the group R or a mono R-substituted phenyl; provided that there is at least one R group or mono R-substituted phenyl on the naphtho or indeno portion of the naphthopyran. The R group may be represented by the general formula:

or

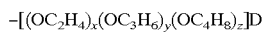

wherein —A is —C(O)— or —$CH_2$—, and D is a polymerizable group, i.e., any functional group capable of participating in a polymerization reaction. Polymer forming methods in which the compounds of the present invention may participate include radical polymerization, and such other polymerization processes as are described in *Ullmann's Encyclopedia of Industrial Chemistry*, "Polymerization Processes", Vol. 21A, pp 305 to 428, which disclosure is incorporated herein by reference. The polymerizable groups may be selected from the group consisting of hydroxy, (meth)acryloxy, and epoxy, e.g., oxiranylmethyl. When there are 2 or more polymerizable groups on the naphthopyran, they may be the same or different.

The group, —$(OC_2H_4)_x$—, represents poly(ethylene oxide); —$(OC_3H_6)_y$—, represents poly(propylene oxide); and, —$(OC_4H_8)_z$—, represents poly(butylene oxide). When used in combination, the poly(ethylene oxide), poly(propylene oxide) and poly(butylene oxide) groups of R may be in a random or block order within the R moiety. The letters x, y and z are each a number between 0 and 50 and the sum of x, y and z is between 1 and 50. The sum of x, y and z may be any number that falls within the range of 1 to 50, e.g., 1, 2, 3 . . . 50. The sum may also range from any lower number to any higher number within the range of 1 to 50, e.g., 6 to 50, 31 to 50. The numbers for x, y, and z are average values and can be partial numbers, e.g., 9.5.

Alternatively, the substituents $R_1$, $R_1'$, $R_2$, each $R_3$, $R_4$, $R_5$ or $R_6$ in graphic formulae I, II and III may be a group other than R or mono R-substituted phenyl provided that at least one of such substituents is the R group or mono R-substituted phenyl. $R_1$ may be hydrogen, $C_1$-$C_3$ alkyl or the group, —C(O)W, W being —$OR_7$, —$N(R_8)R_9$, piperidino or morpholino, wherein $R_7$ is allyl, $C_1$-$C_6$ alkyl, phenyl, mono($C_1$-$C_6$)alkyl substituted phenyl, mono ($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono ($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl; $R_8$ and $R_9$ are each selected from the group consisting of $C_1$-$C_6$ alkyl, $C_5$-$C_7$ cycloalkyl, phenyl and mono- or di-substituted phenyl, said phenyl substituents being selected from $C_1$-$C_6$ alkyl and $C_1$-$C_6$ alkoxy, and said halo substituent being chloro or fluoro. $R_1'$ is the same as $R_1$ except that $R_1'$ is not hydrogen.

$R_2$ and each $R_3$ and $R_4$ may be selected from the group consisting of hydrogen, $C_1$-$C_6$ alkyl, $C_3$-$C_7$ cycloalkyl, phenyl, mono- or di-substituted phenyl and the groups —$OR_{10}$ and —$OC(O)R_{10}$, wherein $R_{10}$ is $C_1$-$C_6$ alkyl, phenyl($C_1$-$C_3$)alkyl, mono($C_1$-$C_6$)alkyl substituted phenyl ($C_1$-$C_3$)alkyl, mono($C_1$-$C_6$)alkoxy substituted phenyl ($C_1$-$C_3$)alkyl, $C_1$-$C_6$ alkoxy($C_2$-$C_4$)alkyl, $C_3$-$C_7$ cycloalkyl or mono($C_1$-$C_4$)alkyl substituted $C_3$-$C_7$ cycloalkyl, n is selected from the integers 0, 1 and 2 and said phenyl substituents are the same as for $R_1$.

$R_5$ and $R_6$ may together form an oxo group, a spirocarbocyclic ring containing 3 to 6 carbon atoms or a spiro-heterocyclic group containing 1 or 2 oxygen atoms and 3 to 6 carbon atoms including the spirocarbon atom and both rings may be benz-annelated with one or two benzene groups. Examples of the spiro-carbocyclic ring substituents include spirofluoreno, spirocyclopropyl, spirocyclobutyl, spirocyclopentyl, spirocyclohexyl, spiroindan-1-yl, spiroindan-2-yl, etc. Examples of the spiro-heterocyclic group include spiroxantheno and compounds which may be represented by the expression (—O—($C_2$-$C_5$ alkanediyl)—O—), e.g., spiro-1,3-dioxolane-2, spiro-1,3-dioxane-2, etc., or spirolactones, such as butyrolactone, propiolactone, etc. Alternatively, $R_5$ and $R_6$ may each be hydrogen, hydroxy, $C_1$-$C_6$ alkyl, $C_3$-$C_7$ cycloalkyl, allyl, phenyl, mono-substituted phenyl, benzyl, mono-substituted benzyl, chloro, fluoro, the group —C(O)X, wherein X is hydroxy, $C_1$-$C_6$ alkyl, $C_1$-$C_6$ alkoxy, phenyl, mono-substituted phenyl, amino, mono($C_1$-$C_6$)alkylamino, or di($C_1$-$C_6$)alkylamino, e.g., dimethyl amino, methyl propyl amino, etc., or $R_5$ and $R_6$ may each be the group, —$OR_{11}$, wherein $R_{11}$ is $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, the group, —$CH(R_{12})Y$, wherein $R_{12}$ is hydrogen or $C_1$-$C_3$ alkyl and Y is CN, $CF_3$, or $COOR_{13}$, and $R_{13}$ is hydrogen or $C_1$-$C_3$ alkyl, or $R_{11}$ is the group, —C(O)Z, wherein Z is hydrogen, $C_1$-$C_6$ alkyl, $C_1$-$C_6$ alkoxy, the unsubstituted, mono- or di-substituted aryl groups, phenyl or naphthyl, phenoxy, mono- or di-($C_1$-$C_6$)alkyl substituted phenoxy, mono- or di-($C_1$-$C_6$)alkoxy substituted phenoxy, mono- or di-($C_1$-$C_6$)alkoxy substituted phenoxy, amino, mono ($C_1$-$C_6$)alkylamino, di($C_1$-$C_6$)alkylamino, phenylamino, mono- or di($C_1$-$C_6$)alkyl substituted phenylamino, or mono- or di-($C_1$-$C_6$)alkoxy substituted phenylamino, each of the aforedescribed phenyl, benzyl and aryl group substituents being $C_1$–$C_6$ alkyl or $C_1$–$C_6$ alkoxy.

B is mono R-substituted phenyl represented by the ollowing graphic formula IV:

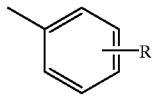

IV wherein the group R is the same as previously described.

B' is selected from the group consisting of:(a) the unsubstituted, mono-, di- and tri-substituted aryl groups, phenyl and naphthyl; (b) 9-julolidinyl and the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (a) and (b) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, amino, mono($C_1$–$C_6$)alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro, each aryl group described for said aryl or heteroaromatic substituent being phenyl or naphthyl; (c) the unsubstituted or mono-substituted groups, pyrazolyl, imidazolyl, pyridyl, pyrazolinyl, imidazolinyl, pyrrolinyl, phenothiazinyl, phenoxazinyl, phenazinyl or acridinyl, each of said substituents for said groups in (c) being selected from the group consisting of $C_1$–$C_6$ alkyl, $C_1$–$C_6$ alkoxy, phenyl, fluoro, chloro and bromo; (d) monosubstituted phenyl, having a substituent at the para position that is the linking group, —$(CH_2)_t$— or —O—$(CH_2)_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran; (e) the groups represented by the following graphic formulae VA and VB:

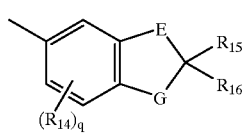

VA

-continued

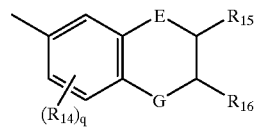

VB wherein E is carbon or oxygen and G is oxygen or substituted nitrogen, provided that when G is substituted nitrogen, E is carbon, said nitrogen substituents being selected from the group consisting of hydrogen, $C_1$–$C_6$ alkyl and $C_2$–$C_6$ acyl; each $R_{14}$ is $C_1$–$C_6$ alkyl, $C_1$–$C_6$ alkoxy, hydroxy, chloro or fluoro; $R_{15}$ and $R_{16}$ are each hydrogen or $C_1$–$C_6$ alkyl; and q is the integer 0, 1 or 2; (f) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)-cycloalkyl, chloro($C_3$–$C_6$) cycloalkyl, fluoro($C_3$–$C_6$)cycloalkyl and $C_4$–$C_{12}$ bicycloalkyl; and (g) the group represented by the following graphic formula VC:

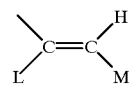

VC wherein L is hydrogen or $C_1$–$C_4$ alkyl and M is selected from the unsubstituted, mono-, and di-substituted members of the group consisting of naphthyl, phenyl, furanyl and thienyl, each of said group substituents in (g) being $C_1$–$C_4$ alkyl, $C_1$–$C_4$ alkoxy, fluoro or chloro.

In graphic formulae I, II and III, $R_1$, $R_1'$, $R_2$, each $R_3$, $R_4$, $R_5$ or $R_6$ may be the same as previously described except that there is at least one R group or mono R-substituted phenyl on the naphthopyran. B and B' may each be selected from the group consisting of the mono R-substituted phenyl represented by graphic formula IV, and the aforedescribed substituents for B' in groups (a), (b), (c), (d), (e), (f) and (g).

Alternatively, B and B' taken together may form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, and cyclododecylidene, saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1] nonan-9-ylidene, bicyclo[4.3.2]undecane, and saturated $C_7$–$C_{12}$ spiro-tricyclic hydrocarbon rings, e.g., tricyclo [2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, fluoro and chloro.

Preferably, $R_1$, $R_1'$, $R_2$, each $R_3$, $R_4$, $R_5$, $R_6$, B and B' are each the same substituents as described in the previous paragraphs and in one preferred embodiment there is only one R group or mono R-substituted phenyl on the naphthopyran.

More preferably, $R_1$, $R_1'$, each $R_3$, $R_4$, $R_5$ or $R_6$ is the group R and $R_2$ is R or a mono R-substituted phenyl. The group, —A, is —C(O)— or —CH$_2$—, and most preferably, —A is —C(O)—. The group, D, is hydroxy or (meth)acryloxy, and most preferably D is hydroxy. The letters x and y are each a number between 0 and 50, z is 0 and the sum of x and y is between 1 and 50, and most preferably, x is a number between 1 and 50, and y and z are each 0.

Preferably, R$_1$ or R$_1$' is the group, —C(O)W, W being —OR$_7$ or —N(R$_8$)R$_9$, wherein R$_7$ is C$_1$–C$_4$ alkyl, phenyl, mono(C$_2$–C$_4$)alkyl substituted phenyl, mono(C$_1$–C$_4$)alkoxy substituted phenyl, phenyl(C$_1$–C$_2$)alkyl, mono(C$_1$–C$_4$)alkyl substituted phenyl(C$_1$–C$_2$)alkyl, mono(C$_1$–C$_4$)alkoxy substituted phenyl(C$_1$–C$_2$)alkyl, mono(C$_1$–C$_4$)alkoxy(C$_2$–C$_3$)alkyl or C$_1$–C$_4$ haloalkyl; R$_8$ and R$_9$ are each selected from the group consisting of C$_1$–C$_4$ alkyl, C$_5$–C$_7$ cycloalkyl, phenyl and mono- or di-substituted phenyl, said phenyl substituents being C$_1$–C$_4$ alkyl or C$_1$–C$_4$ alkoxy, and said halo substituents being chloro or fluoro. More preferably, R$_1$ or R$_1$' is the group, —C(O)W, wherein W is the group, —OR$_7$, and R$_7$ is a C$_1$–C$_3$ alkyl.

Preferably, R$_2$ and each R$_3$ and R$_4$ are selected from the group consisting of hydrogen, C$_1$–C$_3$ alkyl, C$_3$–C$_5$ cycloalkyl, phenyl, mono- or di-substituted phenyl and the group —OR$_{10}$, wherein R$_{10}$ is C$_1$–C$_4$ alkyl, phenyl(C$_1$–C$_2$)alkyl, mono(C$_1$–C$_4$)alkyl substituted phenyl(C$_1$–C$_2$)alkyl, mono(C$_1$–C$_4$)alkoxy substituted phenyl(C$_1$–C$_2$)alkyl, C$_1$–C$_4$ alkoxy(C$_2$–C$_4$)alkyl, C$_5$–C$_7$ cycloalkyl or mono (C$_1$–C$_3$)alkyl substituted C$_5$–C$_7$ cycloalkyl, and the phenyl substituents are C$_1$–C$_3$ alkyl or C$_1$–C$_3$ alkoxy. More preferably, R$_2$ and each R$_3$ and R$_4$ are selected from the group consisting of hydrogen, C$_1$–C$_3$ alkyl, phenyl, mono- or di-substituted phenyl and the group —OR$_{10}$, wherein R$_{10}$ is C$_1$–C$_3$ alkyl and said phenyl substituents are methyl or methoxy.

Preferably, R$_5$ and R$_6$ are each selected from the group consisting of hydrogen, hydroxy, C$_1$–C$_4$ alkyl, C$_3$–C$_6$ cycloalkyl, chloro, fluoro and the group, —OR$_{11}$, wherein R$_{11}$ is C$_1$–C$_3$ alkyl, phenyl(C$_1$–C$_2$)alkyl, mono(C$_1$–C$_3$)alkyl substituted phenyl(C$_1$–C$_3$)alkyl, mono(C$_1$–C$_3$)alkoxy substituted phenyl(C$_1$–C$_3$)alkyl, C$_1$–C$_3$ alkoxy(C$_2$–C$_4$)alkyl, C$_1$–C$_3$ chloroalkyl, C$_1$–C$_3$ fluoroalkyl, the group, —CH(R$_{12}$)Y, wherein R$_{12}$ is hydrogen or C$_1$–C$_2$ alkyl and Y is CN or COOR$_{13}$, R$_{13}$ being hydrogen or C$_1$–C$_2$ alkyl, or R$_{11}$ is the group, —C(O)Z, wherein Z is hydrogen, C$_1$–C$_3$ alkyl, C$_1$–C$_3$ alkoxy, phenyl, naphthyl, the mono-substituted aryl groups, phenyl or naphthyl, phenoxy, mono- or di-(C$_1$–C$_3$) alkyl substituted phenoxy, mono- or di-(C$_1$–C$_3$)alkoxy substituted phenoxy, mono(C$_1$–C$_3$)alkylamino, phenylamino, mono- or di-(C$_1$–C$_3$)alkyl substituted phenylamino, or mono- or di-(C$_1$–C$_3$)alkoxy substituted phenylamino, each of said aryl group substituents being C$_1$–C$_3$ alkyl or C$_1$–C$_3$ alkoxy. More preferably, R$_5$ and R$_6$ are each hydrogen, hydroxy, C$_1$–C$_4$ alkyl or the group, —OR$_{11}$, wherein R$_{11}$ is C$_1$–C$_3$ alkyl.

Preferably, B and B' are each selected from the group consisting of: (a) the mono R-substituted group represented by graphic formula IV; (b) phenyl, mono-substituted and di-substituted phenyl; (c) the unsubstituted, mono- and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in (b) and (c) being selected from the group consisting of hydroxy, aryl, arlyoxy, aryl(C$_1$–C$_3$)alkyl, amino, mono(C$_1$–C$_3$)alkylamino, di(C$_1$–C$_3$)alkylamino, N-(C$_1$–C$_3$)alkylpiperazino, indolino, piperidino, morpholino, pyrryl, C$_1$–C$_3$ alkyl, C$_1$–C$_3$ chloroalkyl, C$_1$–C$_3$ fluoroalkyl, C$_1$–C$_3$ alkoxy, mono(C$_1$–C$_3$)alkoxy(C$_1$–C$_3$) alkyl, chloro and fluoro; (d) the groups represented by graphic formulae VA and VB wherein E is carbon and G is oxygen, R$_{14}$ is C$_1$–C$_3$ alkyl or C$_1$–C$_3$ alkoxy; R$_{15}$ and R$_{16}$ are each hydrogen or C$_1$–C$_4$ alkyl; and q is 0 or 1; (e) C$_1$–C$_4$ alkyl; and (f) the group represented by graphic formula VC, wherein L is hydrogen or methyl and M is phenyl or mono-substituted phenyl, said phenyl substituent being C$_1$–C$_3$ alkyl, C$_1$–C$_3$ alkoxy or fluoro; or B and B' taken together form fluoren-9-ylidene, mono-substituted fluoren-9-ylidene or a member selected from the group consisting of saturated C$_3$–C$_8$ spiro-monocyclic hydrocarbon rings, saturated C$_7$–C$_{10}$ spiro-bicyclic hydrocarbon rings, and saturated C$_7$–C$_{10}$ spiro-tricyclic hydrocarbon rings, said fluoren-9-ylidene substituent being selected from the group consisting of C$_1$–C$_3$ alkyl, C$_1$–C$_3$ alkoxy, fluoro and chloro.

More preferably, B and B' are each selected from the group consisting of: (a) the group represented by graphic formula IV; (b) phenyl, mono- and di-substituted phenyl, preferably substituted in the meta and/or para positions; (c) the unsubstituted, mono- and di-substituted heteroaromatic groups furanyl, benzofuran-2-yl, thienyl and benzothien-2-yl, each of said phenyl and heteroaromatic substituents in (b) and (c) being selected from the group consisting of hydroxy, C$_1$–C$_3$ alkyl, C$_1$–C$_3$ alkoxy, phenyl, indolino, fluoro and chloro; (d) the group represented by graphic formulae VA wherein E is carbon and G is oxygen, R$_{14}$ is C$_1$–C$_3$ alkyl or C$_1$–C$_3$ alkoxy; R$_{15}$ and R$_{16}$ are each hydrogen or C$_1$–C$_3$ alkyl; and q is 0 or 1; or B and B' taken together form fluoren-9-ylidene, adamantylidene, bornylidene, norbornylidene, or bicyclo[3.3.1]nonan-9-ylidene.

Compounds represented by graphic formulae I, II and III may be prepared by the following steps. In Reaction A, an excess of polyethylene glycol represented by general formula VI (wherein x is the same as for group R) or another polyalkylene glycol is reacted with toluenesulfonyl chloride represented by graphic formula VII in the presence of pyridine (PY) at −5° C. to produce the hydroxy (polyethoxy)-p-toluenesulfonate represented by graphic formula VIII. See Bradshaw, J. S., et al, "Synthesis of Macrocyclic Acetals Containing Lipophilic Substituents", Tetrahedron, Vol. 43, No. 19, pp 4271 to 4276, 1987, which disclosure is herein incorporated by reference.

REACTION A

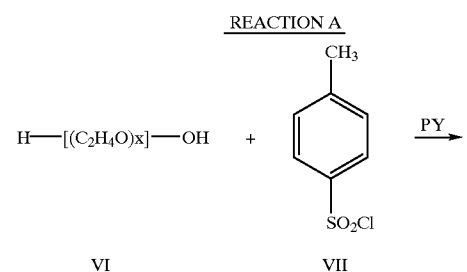

-continued

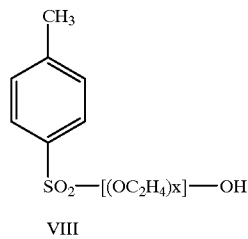

VIII

In Reaction B, the alkoxylated toluenesulfonate represented by graphic formula VIII is reacted with a naphthopyran represented by graphic formula IX in the presence of anhydrous potassium carbonate, acetone and heat to form the hydroxy end-capped alkoxylated naphthopyran of graphic formula IA. Alternatively, halogenated alkoxylated alcohols may be used in place of the alkoxylated toluenesulfonate to alkylate the hydroxy functionality using the aforementioned reaction conditions. Alkylating reactions are further described in *Organic Synthesis*, Vol. 31, pages 90–93, John Wiley & Sons, New York, N.Y.

The compound represented by graphic formula IX may be prepared by coupling a substituted naphthol with a propargyl alcohol. This procedure is described in U.S. Pat. No. 5,458,814, column 5, line 10 to column 7, line 38. The propargyl alcohol may be prepared according to the methods disclosed in U.S. Pat. No. 5,645,767, column 5, line 8 to column 6, line 30. The aforesaid patents are incorporated herein in toto by reference.

A propargyl alcohol containing a 9-julolidinyl or other benzo-fused cyclic amino groups, e.g., indolyl and tetrahydroquinolinyl, may be prepared by the Friedel-Craft's acylation of the material with benzoyl chloride using aluminum chloride as the catalyst. The resulting amino substituted benzophenone may be reacted with sodium acetylide in a solvent such as dimethylformamide to produce a propargyl alcohol containing a benzo-fused cyclic amino substituent. The propargyl alcohol may be used in the hereinafter described coupling reaction to produce a naphthopyran having such a B or B' substituent.

REACTION B

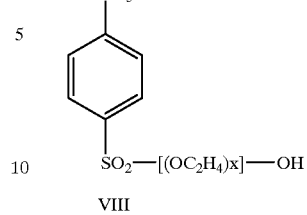

VIII

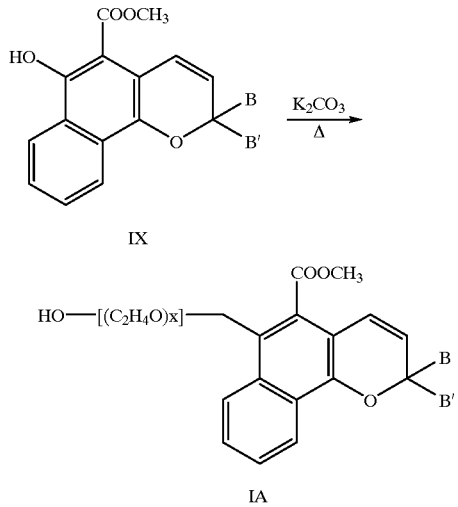

In Reaction C, a substituted naphthoic acid represented by graphic formula X is reacted with a polyethylene glycol represented by general formula VI using concentrated sulfuric acid and heat to form the alkoxylated naphthol represented by graphic formula XI. In graphic formula X, $R_2$ and $R_3$ are as previously defined. The alkoxylated naphthol represented by graphic formula XI is coupled with the propargyl alcohol represented by graphic formula XII to form the alkoxylated naphthopyran represented by graphic formula IB.

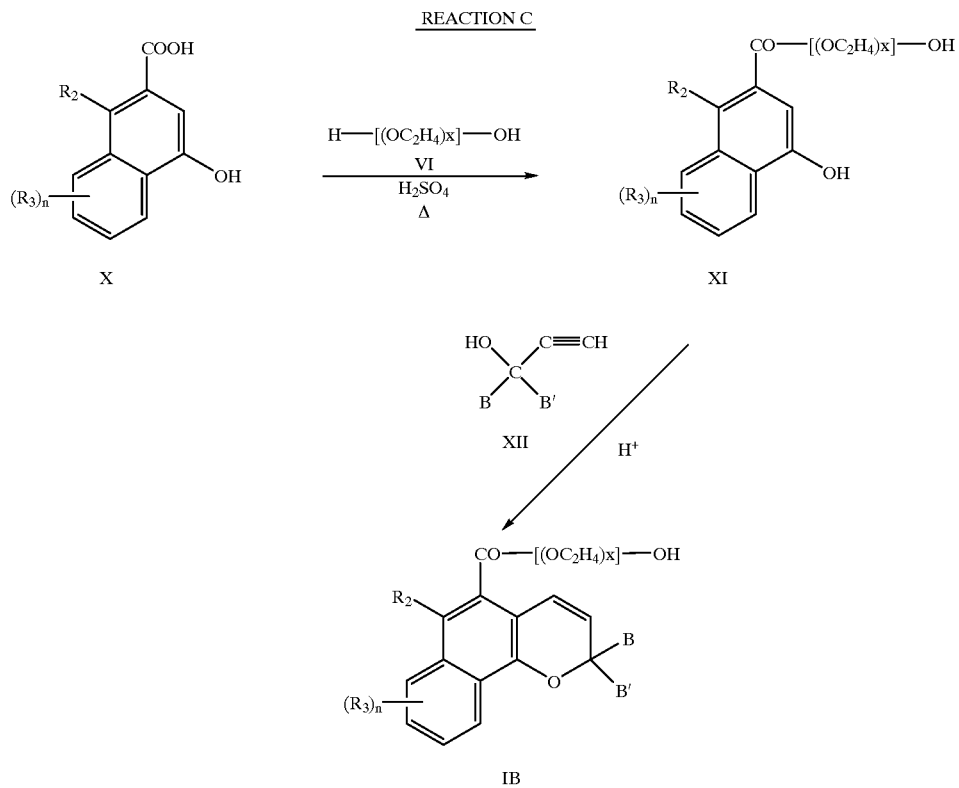

In Reaction D, the alkoxylated toluenesulfonate represented by graphic formula VIII is reacted with a hydroxy substituted benzophenone represented by graphic formula XIII to form the alkoxylated benzophenone represented by graphic formula XIV. The alkoxylated benzophenone is reacted with sodium acetylide in a suitable solvent, such as anhydrous tetrahydrofuran (THF), to form the corresponding propargyl alcohol represented by graphic formula XV. The propargyl alcohol (XV) is coupled with the substituted naphthol of graphic formula XVI to form the alkoxylated naphthopyran represented by graphic formula IIA.

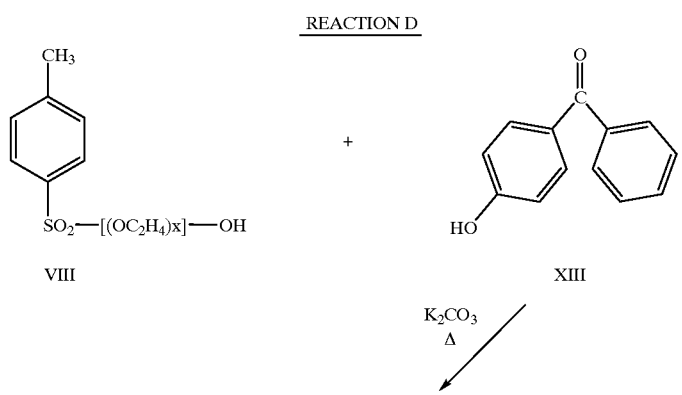

-continued

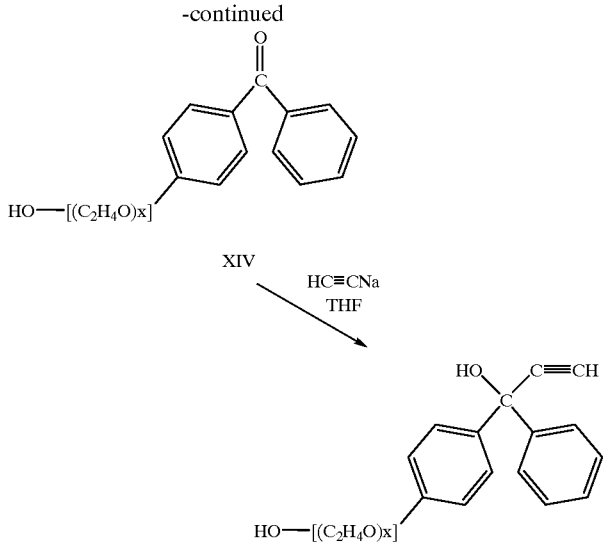

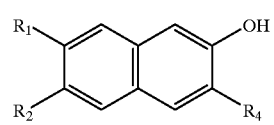

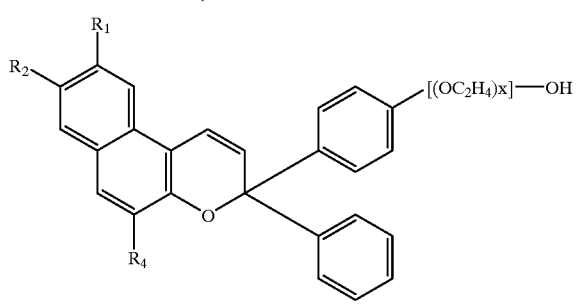

In Reaction E, the hydroxy end-capped alkoxylated toluenesulfonate represented by graphic formula VIII is reacted with a hydroxy substituted acetophenone, benzophenone or benzaldehyde represented by graphic formula XVII to form the corresponding alkoxylated acetophenone, benzophenone or benzaldehyde. The compound of graphic formula XVIII is reacted with an ester of succinic acid such as dimethyl succinate represented by graphic formula XIX. Addition of the reactants to a solvent, e.g., toluene, containing potassium t-butoxide or sodium hydride as the base, yields the Stobbe condensation half ester represented by graphic formula XX. The half ester (XX) undergoes cyclodehydration in the presence of acetic anhydride to form the alkoxylated acetoxynaphthalene represented by graphic formula XXI. This product is reacted with hydrochloric acid (H$^+$)and an anhydrous alcohol such as anhydrous methanol to form the corresponding naphthol represented by graphic formula XXII. The naphthol (XXII) is coupled with a propargyl alcohol represented by graphic formula XII to form the alkoxylated naphthopyran represented by graphic formula IC.

REACTION E

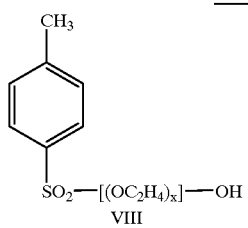

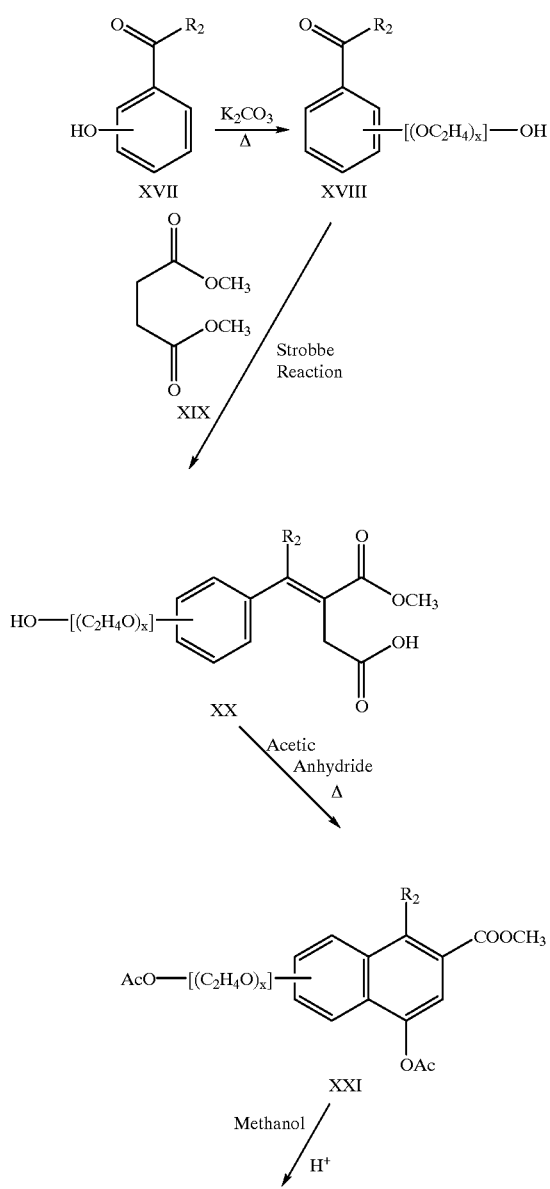

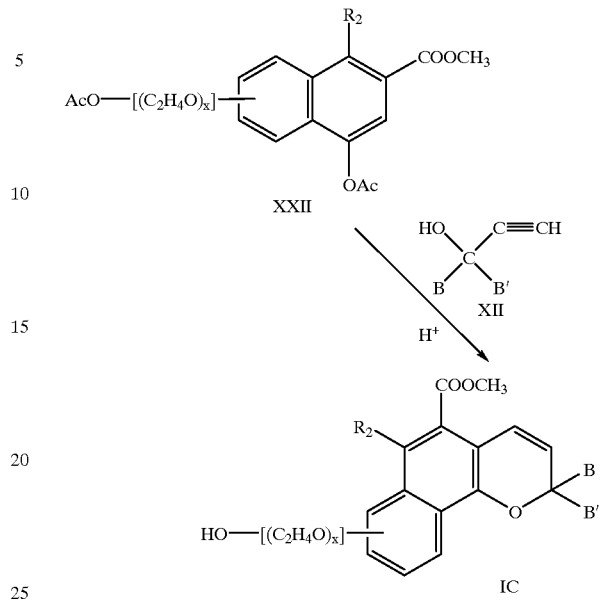

In Reaction F, the alkoxylated benzophenone represented by graphic formula XIV (XVIII with $R_2$ being phenyl) is reacted with an ester of succinic acid such as dimethyl succinate represented by graphic formula XIX. Addition of the reactants to a solvent, e.g., toluene, containing potassium t-butoxide or sodium hydride as the base, yields the Stobbe condensation half esters represented by graphic formulae XXIII and XXIV. The half esters undergo cyclodehydration in the presence of acetic anhydride to form the alkoxylated acetoxynaphthalenes represented by graphic formulae XXV and XXVI. These products are reacted with hydrochloric acid ($H^+$) and an anhydrous alcohol such as anhydrous methanol to form the corresponding naphthols represented by graphic formulae XXVII and XXVIII. The naphthols are coupled with propargyl alcohol represented by graphic formula XII to form the hydroxy end-capped alkoxylated naphthopyrans represented by graphic formula ID and IE. Separations may be performed via chromatography, sequential crystallizations or other separation methods known in the art.

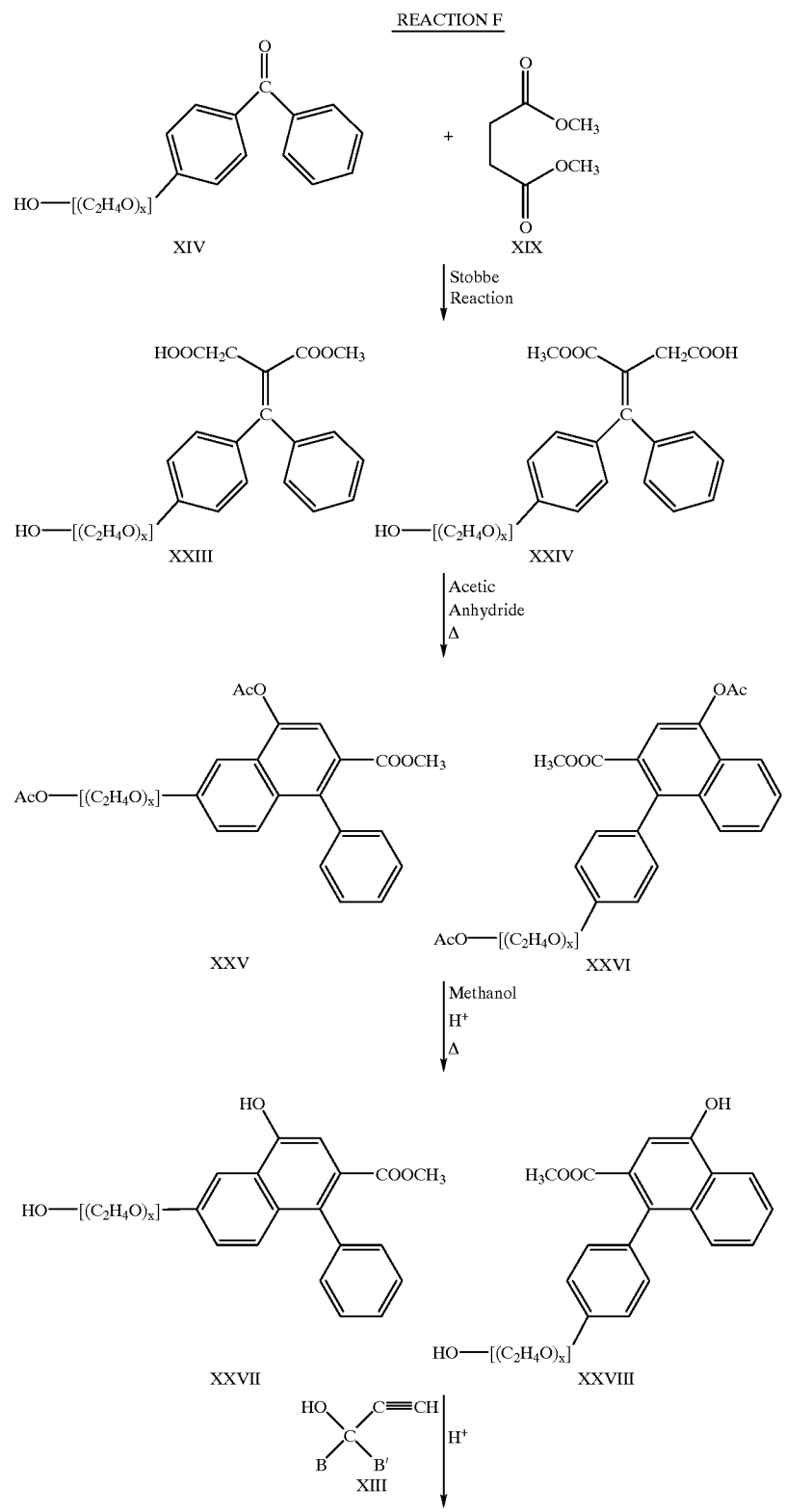

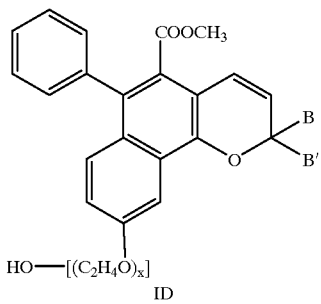

ID

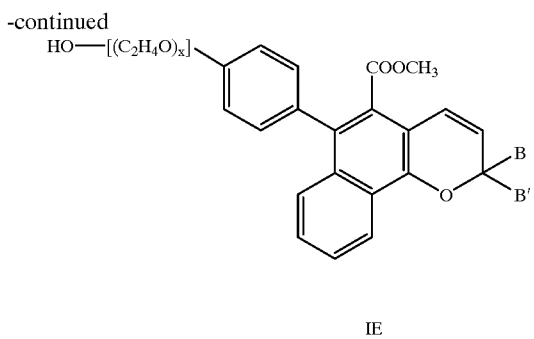

IE

In Reaction G, the compound represented by graphic formula XXIX is reduced with lithium aluminum hydride (LAH) to produce the compound represented by graphic formula XXX. Procedures for preparing the compound of graphic formula XXIX are disclosed in the afore-referenced U.S. Pat. No. 5,645,767. A polyethylene glycol represented by general formula VI (wherein x is the same as for group R) is reacted with the compound of graphic formula XXX using an acid (H$^+$)to form the hydroxy end-capped alkoxylated indeno-fused naphthopyran of graphic formula IIIA.

In Reaction H, the indeno-fused naphthopyran represented by graphic formula XXIX is first reacted with compound XXXI and then cyclized under acidic conditions (H$^+$)to produce the compound represented by graphic formula IIIB. Substituents $R_{15}$ and $R_{16}$ are the same as previously described. Compound XXXI may be prepared from the corresponding phenethyl bromide via reaction with magnesium in ethereal solvents.

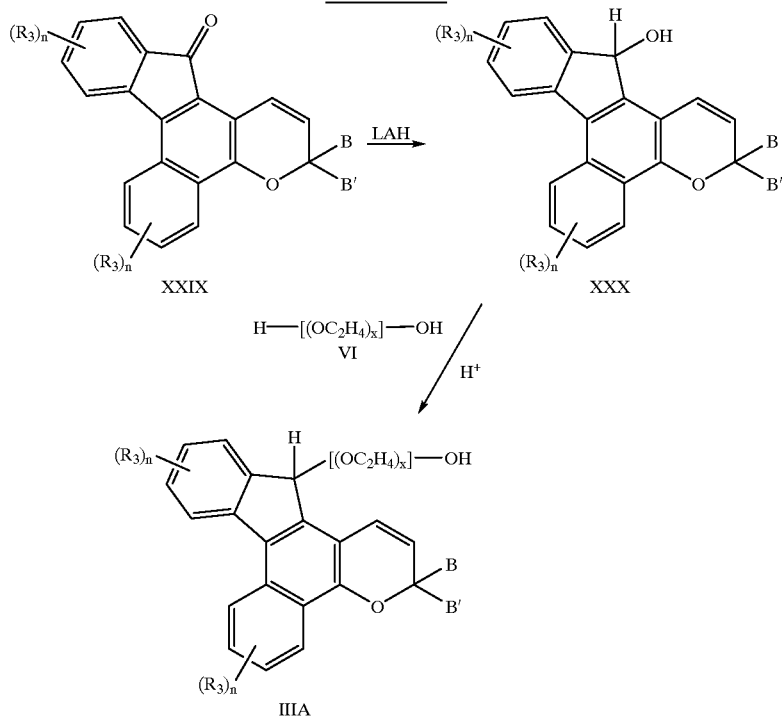

REACTION G

In reactions H and I, the indeno-fused naphthopyrans represented by graphic formula XXIX may be substituted with group R as the $R_3$ substituent. For example, compound XXVII in Reaction F may be cyclized under acidic conditions and coupled with a propargyl alcohol to produce indeno-fused naphthopyrans having the R group at the 6 position. The same may be done to compound XXVIII to produce an indeno-fused naphthopyran having the R group at the 11 position.

REACTION H

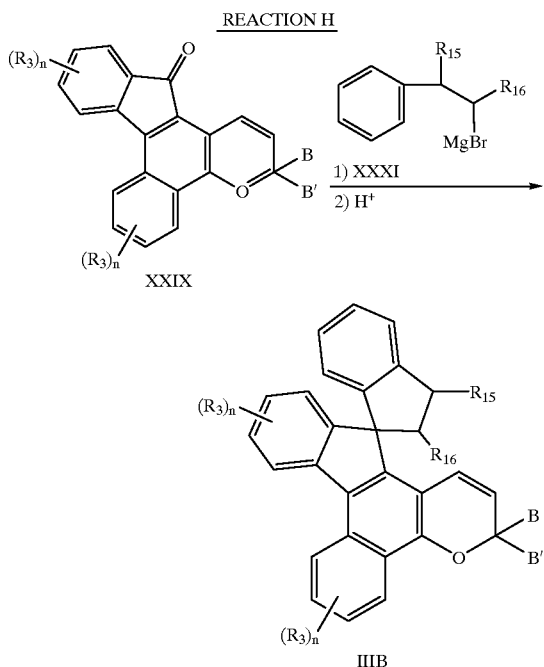

In Reaction I, the indeno-fused naphthopyran represented by graphic formula XXIX is first reacted with compound XXXII and then cyclized under acidic conditions (H⁺) to produce the compound represented by graphic formula IIIC. T in compound XXXII may be selected from the groups, (—O—), (—CH$_2$—), and (—CH=CH—) and m is an integer of from 0 to 2. When T is (—CH$_2$—), m equals 1–2, when T is (—CH=CH—), m equals 1 and when m equals 0, T is a carbon—carbon bond.

REACTION I

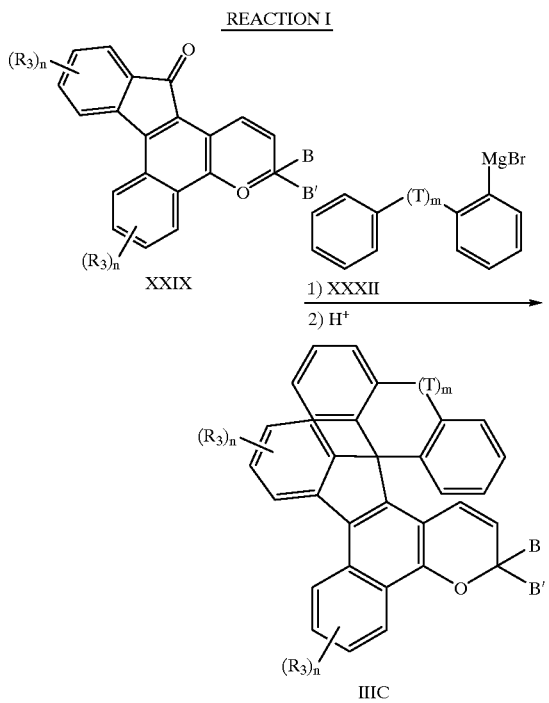

Reactions B, C, D, E, F, G, H and I produce polymerizable naphthopyrans having an end-capped hydroxy group which may be used in reactions to form polyurethane polymers. These hydroxy end-capped naphthopyrans may be reacted with an acrylate, e.g., ethyl methacrylate, in the presence of a catalytic amount of an acid to produce an acryloxy, e.g., methacryloxy, end-capped naphthopyran or with epichlorohydrin in the presence of a base to produce an epoxy end-capped naphthopyran.

The polymerizable polyalkoxylated naphthopyran compounds represented by graphic formulae I, IA, IB, IC, ID, IE, II, IIA, III, IIIA, IIIB and IIIC may be used in those applications in which organic photochromic substances may be employed, such as optical lenses, e.g., vision correcting ophthalmic lenses, contact lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions. As used herein, coating compositions are defined herein to include polymeric coating compositions prepared from materials such as polyurethanes, epoxy resins and other resins used to produce synthetic polymers; paints, i.e., a pigmented liquid or paste used for the decoration, protection and/or the identification of a substrate; and inks, i.e., a pigmented liquid or paste used for writing and printing on substrates, which include paper, glass, ceramics, wood, masonry, textiles, metals and polymeric organic materials. Coating compositions may be used to produce polymeric coatings on optical elements, verification marks on security documents, e.g., documents such as banknotes, passport and drivers licenses, for which authentication or verification of authenticity may be desired.

Depending on the extent of alkoxylation and the polymerizable group used, the photochromic compounds of the present invention may be soluble in water, water soluble polymers or water containing polymers. Soluble is defined as miscible to the extent of at least 1 gram per liter. The water solubility of some of the photochromic compounds of the present invention offers handling and processing advantages not achieved by water insoluble photochromic compounds. In particular, the use of hazardous organic solvents as carriers for photochromic compounds is avoided. Also avoided is the use of such solvents in cleaning excess photochromic material from the surface of polymeric substrates after an imbibition or transfer process.

The 2H-naphtho-[1,2-b]pyrans represented by graphic formula I exhibit color changes from colorless to colors ranging from yellow to red/purple. The 3H-naphtho[2,1-b] pyrans represented by graphic formula II exhibit color changes from colorless to colors ranging from yellow to orange and red. The indeno[2,1-f]naphtho[1,2-b]pyrans represented by graphic formulae III exhibit color changes from colorless to colors ranging from orange to blue/gray.

Examples of contemplated naphthopyrans within the scope of the invention are the following:

(a) 2,2-bis(4-methoxyphenyl)-5-(2-hydroxyethoxycarbonyl)-6-phenyl-[2H]-naphtho[1,2-b]pyran;

(b) 2,2-bis(4-methoxyphenyl)-5-(2-(2-hydroxyethoxy)ethoxycarbonyl)-6-phenyl-[2H]-naphtho[1,2-b]pyran;

(c) 2,2-bis(4-methoxyphenyl)-5-(2-(2-(2-hydroxyethoxy)ethoxy)ethoxycarbonyl)-6-phenyl-[2H]naphtho[1,2-b]pyran;

(d) 2,2-bis(4-methoxyphenyl)-5-(2-(2-(2-(2-hydroxyethoxy)ethoxy)ethoxy)ethoxycarbonyl)-6-phenyl-[2H]-naphtho[1,2-b]pyran;

(e) 2,2-bis(4-methoxyphenyl)-5-methoxycarbonyl-6-(2-hydroxyethoxy)ethoxy-[2H]-naphtho[1,2-b]pyran;

(f) 2-(4-(2-(2-hydroxyethoxy)ethoxy)ethoxyphenyl)-2-phenyl-5-methoxycarbonyl-6-methyl-9-methoxy-[2H]-naphtho[1,2-b]pyran;

(g) 2,2-bis(4-methoxyphenyl)-5-methoxycarbonyl-6-phenyl-9-(2-hydroxyethoxy)-[2H]-naphtho[1,2-b]pyran;

(h) 2,2-bis(4-methoxyphenyl)-5-methoxycarbonyl-6-(4-(2-hydroxyethoxy)phenyl)-[2H]-naphtho[1,2-b]pyran;

(i) 2-phenyl-2-(4-(2-(2-methylprop-2-enoyloxy)ethoxy)phenyl)-5-(methoxycarbonyl)-6-(2-(2-methylprop-2-enoxyloxy)ethoxy)-[2H]-naphtho[1,2-b]pyran;

(j) 2,2,6-triphenyl-5-(2-(2-(2-(2-methylprop-2-enoxyloxy)ethoxy)ethoxy)ethoxycarbonyl)-[2H]-naphtho[1,2-b]pyran;

(k) 2,2,6-triphenyl-5-(2-(2-(2-(oxiran-2-ylmethoxy)ethoxy)ethoxy)ethoxycarbonyl)-[2H]-naphtho[1,2-b]pyran;

(l) 3,3-di(4-methoxyphenyl)-6,11,13-trimethyl-13-(2-(2-hydroxyethoxy)ethoxy)-indeno[2,1-f]naphtho[1,2-b]pyran;

(m) 3,3-di(4-methoxyphenyl)-6,11,13-trimethyl-13-(2-(2-(2-hydroxyethoxy)ethoxy)ethoxy)ethoxy)-indeno[2,1-f]naphtho[1,2-b]pyran;

(n) 3,3-bis(4-methoxyphenyl)-9-methoxycarbonyl-8-(2-hydroxyethoxy)ethoxy-[3H]-naphtho[2,1-b]pyran; and (o) 3-(4-(2-(2-hydroxyethyl)ethoxy)ethoxyphenyl)-3-phenyl-9-methoxycarbonyl-8-methoxy-[3H]-naphtho[2,-1-b]pyran.

It is contemplated that the photochromic naphthopyrans of the present invention may each be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers (or substances containing the same) and which color when activated to an appropriate hue.

The complementary organic photochromic materials may include other polymerizable photochromic compounds, such as those disclosed in U.S. Pat. Nos. 4,719,296; 5,166,345; 5,236,958; 5,252,742; 5,359,085; and 5,488,119. Further examples of complementary organic photochromic compounds include other naphthopyrans and indenonaphthopyrans, chromenes and oxazines, substituted 2H-phenanthro[4,3-b]pyran and 3H-phenanthro[1,2-b]pyran compounds, benzopyran compounds having substituents at the 2-position of the pyran ring and mixtures of such photochromic compounds. Such photochromic compounds are described in U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,981; 5,274,132; 5,384,077; 5,405,958; 5,429,774; 5,458,814; 5,466,398; 5,514,817; 5,552,090; 5,552,091; 5,565,147; 5,573,712; 5,578,252; 5,637,262; 5,645,767; 5,656,206; 5,658,500; 5,658,501; 5,674,432 and 5,698,141. Spiro(indoline)pyrans are also described in the text, *Techniques in Chemistry*, Volume III, "Photochromism", Chapter 3, Glenn H. Brown, Editor, John Wiley and Sons, Inc., New York, 1971.

Other complementary photochromic substances contemplated are metal-dithiozonates, e.g., mercury dithizonates, which are described in, for example, U.S. Pat. No. 3,361,706; and fulgides and fulgimides, e.g., the 3-furyl and 3-thienyl fulgides and fulgimides, which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

The photochromic compounds of the present invention may be associated with a polymeric organic host material or other substrate by various means. They may be incorporated, i.e., dissolved and/or dispersed, into the host material, polymerized with other components of the host material, and/or incorporated into a coating applied to a substrate, e.g., a polymeric coating applied to one surface of the polymeric organic host material.

Other than where otherwise indicated, all numbers expressing values, such as, wavelengths, quantities of ingredients or reaction conditions used herein are to be understood as modified in all instances by the term "about"

Each of the photochromic substances described herein may be used in amounts (or in a ratio) such that an organic host material or substrate to which the photochromic compounds or mixture of compounds is associated, exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe colors may be found in U.S. Pat. No. 5,645,767 column 12, line 66 to column 13, line 19.

The amount of the photochromic naphthopyrans to be applied to or incorporated into a coating composition or host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic compounds. Typically, the more photochromic compound applied or incorporated, the greater is the color intensity up to a certain limit.

The relative amounts of the aforesaid photochromic compounds used will vary and depend in part upon the relative intensities of the color of the activated species of such compounds, the ultimate color desired and the method of application to the host material or substrate. Generally, the amount of total photochromic compound incorporated into or applied to a photochromic optical host material may range from about 0.05 to about 1.0, e.g., from 0.1 to about 0.45, milligrams per square centimeter of surface to which the photochromic compound is incorporated or applied. The amount of photochromic material incorporated into a coating composition may range from 0.1 to 40 weight percent based on the weight of the liquid coating composition.

The photochromic naphthopyrans of the present invention may be associated with the host material by various methods described in the art. See, for example, column 13, lines 40 to 58 of U.S. Pat. No. 5,645,767. Aqueous or organic solutions of the photochromic compounds may be used to incorporate the photochromic compounds into a polymeric organic host material or other materials such as textiles and polymeric coating compositions. Polymeric coating compositions may be applied to the substrate using a coating process such as that described in U.S. Pat. No. 3,971,872, the disclosure of which is incorporated herein by reference.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029, which is incorporated herein by reference. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Most preferably, the polymeric organic host material is a solid transparent or optically clear material, e.g., materials suitable for optical applications, such as plano, ophthalmic and contact lenses, windows, automotive transparencies, e.g., windshields, aircraft transparencies, plastic sheeting, polymeric films, etc.

Examples of polymeric organic host materials which may be used with the photochromic compounds described herein include: polymers, i.e., homopolymers and copolymers, of the bis(allyl carbonate) monomers, diethylene glycol dimethacrylate monomers diisopropenyl benzene monomers, ethoxylated bisphenol A dimethacrylate monomers, ethylene glycol bismethacrylate monomers, poly (ethylene glycol) bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly(methyl methacrylate), poly(oxyalkylene)dimethacrylate, poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polythiourethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No. 5,753,146, column 8, line 62 to column 10, line 34, which disclosure is incorporated herein by reference.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear coatings and polymerizates, i.e., materials suitable for optical applications, such as for example lenses, i.e., plano, ophthalmic and contact lenses. Optically clear polymerizates may have a refractive index that may range from about 1.48 to about 1.75, e.g., from about 1.495 to about 1.66.

Specifically contemplated are polymerizates of optical resins sold by PPG Industries, Inc. under the CR-designation, e.g., CR-307 and CR-407, and polymerizates prepared for use as hard or soft contact lenses. Methods for producing both types of contact lenses are disclosed in U.S. Pat. No. 5,166,345, column 11, line 52, to column 12, line 52, which disclosure is incorporated herein by reference. Additional polymerizates contemplated for use with the photochromic polyalkoxylated naphthopyrans of the present invention are polymerizates used to form soft contact lenses with high moisture content described in U.S. Pat. No. 5,965,630 and extended wear contact lenses described in U.S. Pat. No. 5,965,631, both disclosures of which are incorporated herein by reference.

The present invention is more particularly described in the following examples which are intended as illustrative only, since numerous modifications and variations therein will be apparent to those skilled in the art.

EXAMPLE 1

Step 1

Ethylene glycol, 10 milliliters (mL), and concentrated sulfuric acid, 0.1 gram, were added to a reaction flask containing 1-phenyl-4-hydroxy-2-naphthoic acid, 0.5 gram. The 1-phenyl-4-hydroxy-2-naphthoic acid used, was produced by the process described in Steps 1–4 of Example 1 in U.S. Pat. No. 5,645,767. The reaction mixture was heated to and maintained at 90° C. for approximately 24 hours. After cooling to room temperature, the reaction mixture was poured slowly into 100 mL of water with vigorous mixing. A yellowish-white solid precipitated. The solid was filtered, washed with copious amounts of water and air dried to obtain 0.52 gram of product. A nuclear magnetic resonance (NMR) showed the product to have a structure consistent with 1-phenyl-2-(2-hydroxyethoxycarbonyl)-4-naphthol.

Step 2

1-Phenyl-2-(2-hydroxyethoxycarbonyl)-4-naphthol, from Step 1 and 1.1 equivalents of 1,1-bis(4-methoxyphenyl)-2-propyn-1-ol were added to a reaction flask. Toluene, 100 mL, was added and the reaction mixture was stirred at room temperature. A catalytic amount of dodecylbenzene sulfonic acid (approximately 50 milligrams (mg)) was added, and the resulting brownish-red mixture was stirred at room temperature for 3 hours. The toluene layer was separated and washed carefully with saturated sodium bicarbonate solution. After removing the solvent, toluene, under vacuum, a brownish-red oil was obtained. The oil was purified using silica-gel column chromatography. The eluant was a 1:1.5 mixture of ethyl acetate:hexane. A reddish-brown oil was isolated which foamed upon drying under vacuum. NMR analysis showed the product to have a structure consistent with 2,2-bis(4-methoxyphenyl)-5-(2-hydroxyethoxycarbonyl)-6-phenyl-[2H]-naphtho[1,2-b]pyran.

EXAMPLE 2

Step 1

The procedure of Step 1 of Example 1 was followed except for the following: diethylene glycol was used in place of ethylene glycol; the reaction mixture was poured into water and extracted with ethyl acetate; the ethyl acetate extracts were combined and dried over anhydrous sodium sulfate; and the solvent, ethyl acetate, was removed under vacuum. The desired product was recovered as a light yellow oil. NMR analysis showed the product to have a structure consistent with 1-phenyl-2-(2-(2-hydroxyethoxy)-ethoxycarbonyl)-4-naphthol.

Step 2

The procedure of Step 2 of Example 1 was followed using the product of Step 1 of this Example 2; and a 1:1 mixture of ethyl acetate:hexane was the eluant. The desired product was isolated as a reddish-brown oil. NMR analysis showed the product to have a structure consistent with 2,2-bis(4-methoxyphenyl)-5-(2-(2-hydroxyethoxy)-ethoxycarbonyl)-6-phenyl-[2H]-naphtho[1,2-b]pyran.

EXAMPLE 3

Step 1

The procedure of Step 1 of Example 2 was followed except for the following: triethylene glycol was used in place of diethylene glycol; the reaction mixture was heated for four hours at approximately 180° C.; chloroform was used in place of ethyl acetate; and the separated organic layer was washed with water, 200 mL, aqueous sodium bicarbonate, 200 mL, and finally with dilute aqueous hydrochloric acid, 200 mL. The resulting oil, approximately 5 grams, containing 1-phenyl-2-(2-(2-(2-hydroxyethoxy)ethoxy)ethoxycarbonyl)-4-naphthol was used in the next step without further purification.

Step 2

The product of Step 1 and 1,1-bis(4-methoxyphenyl)-2-propyn-1-ol, 5 grams, were added to a reaction flask containing 200 mL of toluene and stirred. A catalytic amount of p-toluenesulfonic acid (about 100 mg) was added. The resulting mixture was heated on a steam bath at about 100° C. for 1.5 hours, cooled to room temperature and stirred overnight. The solvent, toluene, was removed under vacuum. The resulting residue was dissolved into a minimal amount of a chloroform:ethylacetate eluant (3:1 on a volume basis) and chromatographed in a silica gel column yielding 3.5 grams of an oil recovered as an expanded foam. NMR analysis showed the product to have a structure consistent with 2,2-bis(4-methoxyphenyl)-5-(2-(2-(2-hydroxy-ethoxy)ethoxy)ethoxy-carbonyl)-6-phenyl-[2H]naphtho[1,2-b]pyran.

EXAMPLE 4

Step 1

The procedure of Step 1 of Example 2 was followed except that tetraethylene glycol was used in place of diethylene glycol. NMR analysis showed the product to have a structure consistent with 1-phenyl-2-(2-(2-(2-(2-hydroxy-ethoxy)ethoxy)ethoxy)ethoxycarbonyl)-4-naphthol.

Step 2

The procedure of Step 2 of Example 1 was followed using the product of Step 1 of this Example 4; and a 4:1 mixture of ethyl acetate:hexane was the eluant. The desired product was isolated as a reddish-brown oil. NMR analysis showed the product to have a structure consistent with 2,2-bis(4-methoxyphenyl)-5-(2-(2-(2-(2-hydroxyethoxy)ethoxy)ethoxy)ethoxycarbonyl)-6-phenyl-[2H]-naphtho [1,2-b] pyran.

EXAMPLE 5

2,2-Bis(4-methoxyphenyl)-5-methoxycarbonyl-6-hydroxy-[2H]-naphtho[1,2-b]pyran (Example 1 of U.S. Pat. No. 5,458,814), 3.7 grams, 2-(2-chloroethoxy)ethanol, 5 grams, sodium iodide, 1.2 grams, and anhydrous potassium carbonate, 1.4 grams, were added to a reaction flask containing 40 ml of N,N-dimethylformamide. The reaction mixture was stirred under a nitrogen atmosphere and heated to and maintained at 80° C. for four hours. The reaction mixture was cooled to room temperature, and ethyl acetate, 250 mL, and then water, 300 mL, were added to it. The aqueous layer was separated and extracted with ethyl acetate three times, each with 150 mL. The ethyl acetate extracts were combined and washed carefully with water, three times, each with 300 mL, and then dried over anhydrous sodium sulfate. Removal of the solvent, ethyl acetate, under vacuum yielded a red oil. The oil was dissolved in a minimal amount of chloroform and chromatographed on a silica-gel column using a mixture, based on percent volume, of 50% chloroform, 40% ethyl acetate, and 10% hexane as the eluant. A red oil, 2.1 grams, was isolated which foamed upon drying under vacuum. NMR analysis showed the product to have a structure consistent with 2,2-bis(4-methoxyphenyl)-5-methoxycarbonyl-6-(2-hydroxyethoxy)ethoxy-[2H]-naphtho[1,2-b]pyran.

EXAMPLE 6

Step 1

4-Hydroxybenzophenone, 19.8 grams, sodium iodide, 4.5 grams, and anhydrous potassium carbonate, 27.6 grams, were added to a reaction flask containing 50 mL of N,N-dimethylformamide. The reaction mixture was stirred under a nitrogen atmosphere and heated to 100° C. A solution of 2-(2-(2-chloroethoxy)ethoxy)-ethanol, 18.5 grams, in 20 ml of N,N-dimethylformamide was added dropwise over a one hour period.

Afterwards, the reaction temperature was maintained at 100° C. for three hours. The reaction mixture was cooled to room temperature. Ethyl acetate, 300 mL, and then 400 mL of water were added to the reaction mixture. The aqueous layer was separated and extracted with ethyl acetate, two times, each with 150 mL. The ethyl acetate extracts were combined and washed carefully with water, two times with 300 mL each time, and then dried over anhydrous sodium sulfate. Solvent removal under vacuum yielded a light yellow liquid. NMR analysis showed the product to have a structure consistent with 4-(2-(2-hydroxyethoxy)ethoxy) ethoxy benzophenone. This product was utilized in the next step without further purification.

Step 2

The product of Step 1, 13.2 grams, and N,N-dimethylformamide saturated with acetylene, 150 mL, was added to a reaction flask. The reaction mixture was stirred using a mechanical stirrer at room temperature under a nitrogen atmosphere. Sodium acetylide in xylene/mineral oil, 28 grams of an 18 weight percent suspension, was added to the reaction flask over a thirty minute period while stirring. After three hours, the reaction mixture was added slowly to 1200 mL of distilled water. The water layer was separated and washed with 300 mL of hexane and extracted with ethyl acetate, three times with 250 mL each time. The ethyl acetate extracts were combined, washed with water, and dried over anhydrous sodium sulfate. The remaining solvents were removed under vacuum to yield a dark brown oil. NMR analysis showed the product to have a structure consistent with 1-(4-(2-(2-hydroxy-ethoxy)ethoxy) ethoxyphenyl)-1-phenyl-2-propyn-1-ol. This product was utilized in the next step without further purification.

Step 3

The procedure of Step 2 of Example 1 was followed except for the following: the product of Step 2 of this Example and 1-methyl-2-methoxycarbonyl-6-methoxy-4-naphthol were used; and the eluant used was a mixture, based on percent volume, of 50% ethyl acetate, 45% chloroform and 5% hexane. NMR analysis showed the product to have a structure consistent with 2-(4-(2-(2-hydroxyethoxy)ethoxy)ethoxyphenyl)-2-phenyl-5-methoxycarbonyl-6-methyl-9-methoxy-[2H]-naphtho[1,2-b]pyran.

EXAMPLE 7

Step 1

4-Hydroxybenzophenone (19.8 grams) and 15 grams of anhydrous potassium carbonate were added to a reaction flask containing 80 mL of N,N-dimethylformamide. The reaction mixture was stirred under a nitrogen atmosphere and heated to 100° C. A solution of 2-bromoethanol (26.3 grams) in 20 mL of N,N-dimethylformamide was added dropwise over a fifteen minute period. After overnight stirring at 100° C., the heating was stopped and the reaction mixture was cooled to room temperature. The reaction mixture was poured slowly accompanied by vigorous stirring into 800 mL of water. A white, pasty solid precipitated out. The solid was filtered and 500 mL of ethyl acetate (500 mL) was added to dissolve the product. The ethyl acetate solution was washed twice with water (300 mL), and then once with saturated sodium chloride solution (400 mL). The solvent, ethyl acetate, was removed under vacuum to obtain 22 grams of a white solid. A nuclear magnetic resonance (NMR) showed the product to have a structure consistent with 4-(2-hydroxyethoxy)-benzophenone. This product was utilized in the next step without further purification.

Step 2

Potassium t-butoxide (9 grams) was added to a reaction flask containing 50 mL of toluene. A solution containing 4-(2-hydroxyethoxy)-benzophenone (12 grams) and dimethyl succinate (8.3 grams) in 100 mL of toluene was added dropwise over a thirty minute period to the reaction flask accompanied by mechanical stirring. The resulting brownish-red solution was heated to reflux temperature under a nitrogen atmosphere. After two hours, the heating was stopped and the reaction mixture was cooled to room temperature. Water (300 mL) was added to the reaction mixture. The aqueous layer was separated and washed once with 200 mL of ethyl acetate. The aqueous layer was neutralized with dilute hydrochloric acid, and then extracted three times with ethyl acetate (200 mL) each time. The combined ethyl acetate extracts were washed once with saturated sodium chloride solution (200 mL), dried over anhydrous sodium sulfate, and then the solvent was removed under vacuum to yield 14.4 grams of a dark brown oil. Mass spectroscopic analysis showed the oil to contain the cis and trans isomers of 4-phenyl-4-(4-(2-hydroxyethoxy)phenyl)-3-methoxycarbonyl-3-butenoic acid as the major product. This product was utilized in the next step without further purification.

Step 3

The mixture of the half-isomers (14.1 grams) from Step 2 was added to a reaction flask containing 30 mL of acetic anhydride and 2.3 grams of sodium acetate. The reaction mixture was heated at reflux temperature under a nitrogen atmosphere. After four hours, the heating was stopped and the reaction mixture was cooled to room temperature. The following were added carefully to the reaction mixture in the order listed: ethyl acetate (300 mL), water (100 mL) and saturated sodium bicarbonate solution (100 mL). The remaining acid was neutralized with solid sodium bicarbonate. The ethyl acetate layer was separated and washed with 300 mL of saturated sodium bicarbonate solution, followed by 200 mL of saturated sodium chloride solution. After drying over anhydrous sodium sulfate, the solvent was removed under vacuum to obtain 12.8 grams of a brown oil containing 1-phenyl-2-methoxycarbonyl-4-acetoxy-6-(2-acetoxyethoxy)-naphthalene and 1-(4-(2-acetoxyethoxy) phenyl)-2-methoxycarbonyl-4-acetoxy-naphthalene. This product was utilized in the next step without further purification.

Step 4

The brown oil (12.2 grams) from Step 3 was added to a reaction flask containing 200 mL of methanol. Concentrated hydrochloric acid (1 mL) was added and the reaction mixture was heated at reflux temperature under a nitrogen atmosphere. After five hours, the heating was stopped and the reaction mixture was cooled to room temperature. The solvent was removed under reduced pressure to yield 11.3 grams of a reddish-brown oil containing 1-phenyl-2-methoxycarbonyl-6-(2-hydroxyethoxy)-4-naphthol and 1-(4-(2-hydroxyethoxy)phenyl)-2-methoxycarbonyl-4-naphthol. This product was utilized in the next step without further purification.

Step 5

The reddish-brown oil (0.7 gram) from Step 4 was added to a reaction flask containing 40 mL of toluene. The mixture was heated to dissolve the reddish-brown oil, and then 0.55 gram of 1,1-bis(4-methoxyphenyl)-2-propyn-1-ol was added to the reaction flask. A catalytic amount (approximately 20 mg) of dodecylbenzenesulfonic acid was added, and the resulting brownish-red mixture was stirred at room temperature under a nitrogen atmosphere. The stirring was stopped after two hours. The toluene layer was separated and washed carefully with saturated sodium bicarbonate solution. After removing the solvent under vacuum, a brownish-red oil was obtained. The oil was purified using preparatory thin layer chromatography on a silica-gel plate. The desired photochromic products were isolated as red oils. When the isolated products on silica gel plates were exposed to ultraviolet radiation (265 Nm), both formed a deeper red color. This activated color faded back to the original color after removal of the UV radiation source. Nuclear magnetic resonance (NMR) showed the first product (designated 7A) to have a structure consistent with 2,2-bis(4-methoxyphenyl)-5-methoxycarbonyl-6-phenyl-9-(2-hydroxyethoxy)-[2H]-naphtho[1,2-b]pyran, and the second product (designated 7B) to have a structure consistent with 2,2-bis(4-methoxyphenyl)-5-methoxycarbonyl-6-(4-(2-hydroxyethoxy)-phenyl)-[2H]-naphtho[1,2-b]pyran.

EXAMPLE 8

Step 1

Potassium t-butoxide (75 grams, 0.67 mole) was added to a reaction flask containing 200 milliliters (mL) of toluene. The reaction flask was equipped with an overhead stirrer, dropping funnel, and a condenser with nitrogen inlet. The contents of the reaction flask was heated to reflux temperature and a mixture of 4,4'-dimethylbenzophenone (105 grams, 0.5 mole), dimethyl succinate (90 grams, 0.62 mole), and toluene (200 grams) was added over a period of one-half hour. The resulting pasty mixture was refluxed an additional two hours, cooled, and about 400 mL of water was added and mixed well. The aqueous layer was separated, acidified with dilute hydrochloric acid, and extracted with 200 mL of toluene. The solvents, toluene and residual t-butanol, were removed on the rotary evaporator to produce a near quantitative yield of crude half-ester, 4,4-di(4-methylphenyl)-3-methoxycarbonyl-3-butenoic acids. This material was not purified further but was used directly in the next step.

Step 2

The crude half-ester from Step 1 was added to a reaction flask containing 200 mL of toluene. Acetic anhydride (100 grams) and anhydrous sodium acetate (15 grams) were added and the mixture was refluxed for 17 hours. The mixture was cooled and the solvent, toluene, was removed on a rotary evaporator. The resulting residue was dissolved in 200 mL of methylene chloride and stirred. Water (200 mL) was added followed by the slow addition of solid sodium carbonate until carbon dioxide evolution ceased. The methylene chloride layer was separated and washed with water. The solvent, methylene chloride, was removed on a rotary evaporator to yield about 100 grams of crystalline solid. The recovered product, 1-(4-methylphenyl)-2-methoxycarbonyl-4-acetoxy-6-methyl naphthalene, had a melting point of 144–146° C.

Step 3

The product from Step 2 (about 100 grams) was added to a reaction flask containing 350 mL of a 10 weight percent aqueous sodium hydroxide solution and 50 mL of methanol. The mixture was refluxed for one hour, cooled, then slowly poured into a beaker containing approximately one liter of cold (approx. 4° C.) dilute hydrochloric acid. About 100 grams of the resulting crystalline product, 1-(4-methylphenyl)-4-hydroxy-6-methyl-2-naphthoic acid, having a melting point of 210–213° C., was collected by vacuum filtration.

Step 4

The product from Step 3 (about 100 grams) was added to a reaction flask containing xylene (250 grams) and 250 grams of a 85 weight percent phosphoric acid solution. The stirred mixture was refluxed in a one liter flask equipped with a Dean-Stark-trap for 20 hours. During this time a solid product formed. The mixture was cooled and 200 mL of water was added. The solid was broken up with a spatula, filtered, and washed successively with water, 5 weight percent aqueous sodium bicarbonate, and water. Ninety grams of the product, 3,9-dimethyl-5-hydroxy-7H-benzo[C]-fluoren-7-one, were recovered by vacuum filtration.

Step 5

The product from Step 4 (10 grams) was added to a reaction flask containing 1,1-di(4-methoxyphenyl)-2-propyn-1-ol (10 grams) and 100 mL of toluene. The resulting mixture was stirred and heated to 50° C., three drops of dodecybenzene sulfonic acid were added, and the reaction mixture was kept at 50° C. for five hours. After the reaction mixture cooled to room temperature, it was filtered and the collected filtrate was washed three times with 5 weight percent aqueous sodium hydroxide. The solvent, toluene, was removed on a rotary evaporator and the desired product crystallized on the addition of acetone to the residue. The solid was vacuum filtered, washed with fresh acetone, and dried, to yield 16 grams of a product having a melting point of 227–229° C. An NMR showed the product to have a structure consistent with 3,3-di(4-methoxyphenyl)-6,11-dimethyl-13-oxo-indeno[2,1-f]naphtho[1,2-b]pyran.

Step 6

The product of Step 5 (10 grams) was added to a reaction flask containing 50 mL of anhydrous tetrahydrofuran. The mixture was cooled in an ice bath and protected from moisture with a nitrogen pad while an excess of methyl Grignard reagent was added to the reaction with stirring. After stirring an additional ten minutes, 200 mL of 5 weight percent aqueous hydrochloric acid was added and the organic layer was separated and washed with water. The solvent, tetrahydrofuran, was removed on a rotary evaporator. The addition of approximately ten milliliters of a 2:1 mixture of hexane:ethyl acetate to the residue caused the crystallization of a non photochromic material. This material was separated by filtration. The filtrate was column chromatographed on silica using a 3:1 mixture of hexane:ethyl acetate as elutant. The desired product, which crystallized from a methanol mixture, was filtered and dried to yield 8 grams of a product having a melting point of 233–235° C. An NMR spectrum showed the product to have a structure consistent with 3,3-di(4-methoxyphenyl)-6,11,13-trimethyl-13-hydroxy-indeno[2,1-f]naphtho[1,2-b]pyran.

Step 7

The product from Step 6 (3.0 grams) was added to a reaction flask containing 100 mL of di(ethylene glycol), 100 mL of chloroform, and 1 mL of 37% hydrochloric acid. The reaction was heated to 50° C. and stirred for 16 hours. The reaction mixture was added to 300 mL of water and an additional 100 mL of chloroform was added. The organic layer was separated, washed with water, filtered, and the solvent, chloroform, was removed on a rotary evaporator. The resulting residue was chromatographed on silica using ethyl acetate as the eluant. The photochromic fractions were combined, the solvent was evaporated, and the desired product was induced to crystallize from a hexane/diethyl ether mixture. The recovered crystals were dried and filtered to yield 2 grams of product. An NMR spectrum showed the product to have a structure consistent with 3,3-di(4-methoxyphenyl)- 6,11,13-trimethyl-13-(2-(2-hydroxyethoxy)ethoxy)-indeno[2,1-f]naphtho[1,2-b]pyran.

EXAMPLE 9

The process of Example 8 was followed except that in Step 7, tetra(ethylene glycol), 100 mL, was used instead of di(ethylene glycol) and 2.7 grams of 3,3-di(4-methoxyphenyl)-6,11,13-trimethyl-13-hydroxy-indeno[2,1-f]naphtho[1,2-b]pyran was used. The recovered crystals were dried and filtered to yield 1 gram of product. An NMR spectrum showed the product to have a structure consistent with 3,3-di(4-methoxyphenyl)-6,11,13-trimethyl-13-(2-(2-(2-(2-hydroxyethoxy)ethoxy)ethoxy)ethoxy)-indeno[2,1-f]naphtho[1,2-b]pyran.

Comparative Example 1 (CE 1)

CE 1 is 2,2-bis(4-methoxyphenyl)-5-methoxycarbonyl-6-phenyl[2H]naphtho[1,2-b]pyran. It may be prepared by following the procedure described for Example 1 of U.S. Pat. No. 5,458,814 using 1-phenyl-4-hydroxy-2-naphthoate in place of methyl-4-dihydroxy-2-naphthoate.

Comparative Example 2 (CE 2)

CE 2 is 2,2-bis(4-methoxyphenyl)-5-methoxycarbonyl-6-methoxy-[2H]-naphtho[1,2-b]pyran. It may be prepared by following the procedure described for Example 2 of U.S. Pat. No. 5,458,814.

Comparative Example 3 (CE 3)

CE 3 is 2-(4-methoxyphenyl)-2-phenyl-5-methoxycarbonyl-6-methyl-9-methoxy-[2H]-naphtho[1,2-b]pyran. This compound was prepared using the procedure described for Step 2 of Example 5 of U.S. Pat. No. 5,458,814 except that 1-methyl-2-methoxycarbonyl-6-methoxy-4-naphthol was used in place of methyl-1,4-dihydroxy-2-naphthoate.

Comparative Example 4 (CE 4)

CE 4 is 3,3-di(4-methoxyphenyl)-6,11,13-trimethyl-3-hydroxy-indeno[2,1-f]naphtho[1,2-b]pyran. It may be repared by following the procedure described for Example 5 of U.S. Pat. No. 5,645,767.

EXAMPLE 10

Part A

Testing was done with the photochromic compounds described in the Examples and the Comparative Examples in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm×6 inches (15.24 cm) ×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60° C. for 16 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were conditioned, i.e., exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 250 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliwatts per square centimeter (mW/$cm^2$). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta OD$) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\% Ta)$, where % Ta is the percent transmittance in the activated state and the logarithm is to the base 10.

The optical properties of the photochromic compounds in the test squares are reported in Table 1. When comparing results, Comparative Example 1 is the corresponding compound of, i.e., should be compared to, Examples 1–4, CE 2 should be compared to Example 5, CE 3 should be compared to Example 6 and CE 4 should be compared to Examples 8 and 9. In each comparison, the Comparative Example compound has the same structure as the Example compound except for the hydroxy end-capped polyalkoxylated substituent. The $\Delta$ OD/Min, which represents the sensitivity of the photochromic compound's response to UV light, was measured over the first five (5) seconds of UV exposure, then expressed on a per minute basis. The saturation optical density ($\Delta$ OD@ Saturation) was taken under identical conditions as the $\Delta$ OD/Min, except UV exposure was continued for 15 minutes. The lambda max (Vis) is the wavelength in nanometers (nm) in the visible spectrum at which the maximum absorption of the activated (colored) form of the photochromic compound in a test square occurs. The lambda max (Vis) wavelength was determined by testing the photochromic test square polymerizates of Part A in a Varian Cary 3 UV-Visible spectrophotometer. The Bleach Rate (T ½) is the time interval in seconds for the absorbance of the activated form of the photochromic compound in the test squares to reach one half the highest absorbance at room temperature (72° F., 22.2° C.) after removal of the source of activating light.

Part C

Further testing was done with the photochromic compounds described in the Examples and the Comparative Examples in the following manner. 0.608 Millimole of each photochromic compound was dissolved in 1.264 grams of N-methyl pyrrolidone (NMP). The resulting photochromic solutions of Comparative Examples 1–3 were each added to 4.0 grams of Polyurethane Coating Composition (PCC) A. PCC A is substantially the same formulation as Example 5 in co-pending U.S. patent application Ser. No. 09/083,376, filed May 22, 1998, except that PCC A does not contain Photochromics No. 1 and 2, TINUVIN 292 stabilizer and additional NMP but it does contain 2.8 weight percent γ-glycidoxypropyltrimethoxysilane, available as SILQUEST A-187 from OSI Specialties, Inc.

The resulting photochromic solutions of Examples 1–6 were each added to 4.387 grams of PCC-B. PCC B is substantially the same as PCC A except that it contains an additional 10 weight percent of VESTANAT B 1358. The additional amount of VESTANAT B 1358 was added to maintain an NCO:OH ratio of 1.2:1.0 since the photochromic compounds of Examples 1–6 contributed additional hydroxyl groups.

Part D

The solutions prepared in Part C were applied via a spincoating method to lenses prepared from CR-39® monomer. The lenses were 76 millimeters in diameter, 2 millimeters thick and were obtained from SOLA Optical USA. Prior to application of the coating, each lens was immersed for 3 minutes in an aqueous potassium hydroxide solution having a normality of about 2.4 that was maintained at a temperature of 55° C. and then rinsed with deionized water twice, by immersion for 3 minutes each time and then rinsed with isopropyl alcohol and air dried. The immersion steps were conducted in a Branson Ultrasonic Model 5200 sonicator. Approximately 200 milligrams of solution was dispensed onto each lens that was spinning at 2000 rpm. The coated lenses were cured for 40 minutes in a convection oven maintained at 140° C.

Part E

The photochromic coated lenses prepared in Part D were subjected to microhardness testing using a Fischerscope HCV, Model H-100 available from Fischer Technology, Inc. The microhardness, measured in Newtons per $mm^2$, of the coated lenses was determined under the conditions of a 100 milliNewton load, 30 load steps and 0.5 second pauses between load steps. Each lens was tested 3 times after the samples were stored in an enclosed chamber having a humidity of less than or equal to 50 percent, e.g., 30 percent, for at least 12 hours before each Fischer microhardness test. The numerical average of those test results is listed in Table 2.

Part F

The photochromic coated lenses prepared in Part D were tested for photochromic response using the procedure described in Part B except for the following: test sample exposure times were increased from 15 to 20 minutes and from 2 to 3 hours, the power output of the optical bench was adjusted to 0.67 $mW/cm^2$ measurements were made when the optical bench temperature was 72° F. (22° C.) and 95° F. (35° C.). When the temperature of 72° F. (22° C.) was used, the lenses were activated for 45 minutes and the ΔOD was measured after the first 30 seconds and then after 45 minutes. When the temperature of 95° F. (35° C.) was used, the lenses were activated for 25 minutes and the ΔOD was measured after the first 30 seconds and then after 25 minutes.

The photochromic response data collected when the optical bench temperature was 72° F. (22° C.) and 95° F. (35° C.) was also used to determine the temperature dependency of the Example compounds compared to the Comparative Examples. These results are reported in Table 3. The temperature dependence (TD) is calculated by using the following formula:

$$\Delta OD 72° F. - \Delta OD 95° F.$$

$$\text{Average } (\Delta OD 72° F. + \Delta OD 95° F.)$$

Fatigue testing was conducted on the coated lenses by exposing the samples to solar simulated radiation in a Weather-Ometer, Model No. Ci 4000 made by the Atlas Electric Devices Co. Immediately prior to exposure in the Weather-Ometer, the coated lenses were stored for 1 hour in a dark chamber maintained at 40° C. and 45% relative humidity. In the Weather-Ometer, the lenses were kept for 65 hours at a temperature of 50° C. and relative humidity of 70% and were exposed to a source of 340 Nm radiation at a dosage level of 0.25 $mW/cm^2$.

The Percent Fatigue was determined by measuring on he optical bench the difference between the change in optical density (ΔOD) of the test lenses before and after fatiguing in the Weather-Ometer and calculating the percent reduction in optical density that the difference represents. Prior to testing on the optical bench, the test lenses were conditioned using the aforedescribed conditioning step. The Percent Fatigue was measured for a specific wavelength using a 520±15 nm band pass filter. Testing on the optical bench was done at a temperature of 100° F. with an exposure interval of 90 sec and a dosage of 1.86 $mW/cm^2$.

The Δb* color values were also determined for the test lenses by subtracting the initial b* color values of the CIELAB color space from the b* values measured after 65 hours of fatigue at 122° F. (50° C.). The b* color values of the CIELAB color space were collected under the conditions of a $D_{65}$ illuminant and a 10 degree observer on a Hunter Ultrascan XE color spectrophotometer. The control of the test conditions and acquisition of data was handled by the Labtech Notebook Pro software and the recommended I/O board. The results of the Fatigue and Ab* color value testing are listed in Table 4. The results of the photochromic response testing at 72° F. and at 95° F. are reported in Tables 5 and 6, respectively.

TABLE 1

| Example Number | (λ) max (VIS) | ΔOD/MIN Sensitivity | ΔOD@ Saturation | Bleach Rate (T 1/2) |
| --- | --- | --- | --- | --- |
| 1 | 521 | 0.21 | 0.19 | 46 |
| 2 | 521 | 0.25 | 0.19 | 42 |
| 3 | 523 | 0.22 | 0.19 | 40 |
| 4 | 520 | 0.22 | 0.21 | 43 |
| 5 | 513 | 0.32 | 0.67 | 115 |
| 6 | 515 | 0.14 | 0.60 | 272 |
| 8 | 570 | 0.29 | 0.50 | 102 |
| 9 | 572 | 0.33 | 0.50 | 94 |
| CE 1 | 518 | 0.18 | 0.22 | 56 |
| CE 2 | 512 | 0.29 | 0.77 | 136 |
| CE 3 | 515 | 0.18 | 0.71 | 279 |
| CE 4 | 570 | 0.78 | 0.73 | 362 |

The results of Table 1 show that the Bleach Rate (T½) of the Example compounds was faster than that of the corresponding Comparative Example compounds, i.e., the T½ of each of Examples 1–4 was faster than that of CE 1, the T½ of Example 5 was faster than that of CE 2, the T½ of Example 6 was faster than that of CE 3 and the T½ of Examples 8 and 9 was faster than that of CE 4. In a comparison of the other parameters tested, the results from the Examples and corresponding Comparative Examples were very similar. The results of Table 1 are for Example compounds that were not polymerized into the sample matrix.

TABLE 2

| Example Number | Microhardness Newtons per mm$^2$ |
|---|---|
| 1 | 118 |
| 2 | 118 |
| 3 | 116 |
| 4 | 110 |
| 5 | 122 |
| 6 | 115 |
| CE 1 | 88 |
| CE 2 | 90 |
| CE 3 | 89 |

The results in Table 2 show that the coatings made with the polymerizable naphthopyrans of Examples 1–6 were harder than those with the non-polymerizable Comparative Example 1–3.

TABLE 3

| Example Number | Temperature Dependency |
|---|---|
| 1 | 0.58 |
| 2 | 0.66 |
| 3 | 0.63 |
| 4 | 0.68 |
| 5 | 0.54 |
| 6 | 0.57 |
| CE 1 | 0.78 |
| CE 2 | 0.64 |
| CE 3 | 0.63 |

The results in Table 3 show that each of the polymerizable Examples 1–6 has a lower value for Temperature Dependency than their corresponding Comparative Examples. This means that the Example Compounds showed less of a decrease in the Δ Optical Density vis-a-vis their corresponding Comparative Example Compounds when comparing test results at 95° F. to 72° F.

TABLE 4

| Example Number | Percent Fatigue | Δb* |
|---|---|---|
| 1 | 15 | 2.6 |
| 2 | 14 | 2.8 |
| 3 | 19 | 2.7 |
| 4 | 16 | 2.5 |
| 5 | 38 | 7.1 |
| 6 | 48 | 5.3 |
| CE 1 | 26 | 4.7 |
| CE 1** | 9 | 2.7 |
| CE 2 | 94 | 2.6 |
| CE 3 | 77 | 8.7 |

**Comparative Example 1 with 1.8 weight percent of TINUVIN 144 a hindered amine light stabilizer (HALS) available from Ciba Geigy.

The results of Table 4 show that the coatings prepared with the polymerizable Example Compounds 1–4 and 6 demostrated less fatigue and a lower Δb* color value than the coating prepared with their corresponding Comparative Examples 1 and 3, respectively. The results for Example Compound 5 as compared to corresponding CE 2 showed less fatigue but a higher Δb*. Coatings prepared with Examples 1–4 had Δb* color values approximately equal to that of a coating prepared with CE 1** containing HALS.

TABLE 5

| Example Number | ΔOD at 30 seconds | ΔOD@ Saturation | Bleach Rate (T 1/2) |
|---|---|---|---|
| 1 | 0.10 | 0.42 | 281 |
| 2 | 0.13 | 0.47 | 207 |
| 3 | 0.13 | 0.46 | 189 |
| 4 | 0.16 | 0.51 | 140 |
| 5 | 0.25 | 1.28 | 430 |
| 6 | 0.19 | 1.41 | 901 |
| CE 1 | 0.29 | 0.64 | 62 |
| CE 2 | 0.38 | 1.29 | 176 |
| CE 3 | 0.34 | 1.61 | 441 |

The results of Table 5 (photochromic response at 72° F.) show that the ΔOD at saturation is lower and there is a decrease in the rate of bleaching, i.e., an increase in the T½ for each of the coatings containing polymerizable Example 1–6 compounds as compared to their corresponding Comparative Examples except for the ΔOD of Example 5 which is roughly equal to that of Comparative Example 2. Also shown by the results is a progressive decrease in the T½ and a progressive increase in ΔOD values for coatings containing Examples 1, 2, 3 and 4. These examples have the same photochromic base compound with varying chain lengths of 1, 2, 3 and 4 ethoxy units, respectively.

TABLE 6

| Example Number | ΔOD at 30 seconds | ΔOD@ Saturation | Bleach Rate (T 1/2) |
|---|---|---|---|
| 1 | 0.08 | 0.23 | 95 |
| 2 | 0.11 | 0.24 | 58 |
| 3 | 0.11 | 0.24 | 55 |
| 4 | 0.14 | 0.25 | 37 |
| 5 | 0.24 | 0.73 | 118 |
| 6 | 0.18 | 0.78 | 211 |
| CE 1 | 0.22 | 0.28 | 16 |
| CE 2 | 0.35 | 0.66 | 48 |
| CE 3 | 0.31 | 0.84 | 106 |

The results of Table 6 (photochromic response at 95° F. show that the ΔOD at saturation is slightly lower and there is an increase in the T½ for the coatings containing polymerizable Example compounds 1–4 and 6 as compared to their corresponding Comparative Examples. The ΔOD of Example 5 is slightly higher than that of corresponding Comparative Example 2. The aforementioned progressive trend with increasing ethoxy chain length of Examples 1–4 is also evident in these results. There is also less of a difference between the ΔOD of the coating containing Example 4 and the Comparative Example 1 coating at 95° F. vis-à-vis the same coatings tested at 72° F.

The present invention has been described with reference to specific details of particular embodiments thereof. It is not intended that such details be regarded as limitations upon the scope of the invention except insofar as to the extent that they are included in the accompanying claims.

We claim:

1. A naphthopyran compound represented by the following graphic formulae:

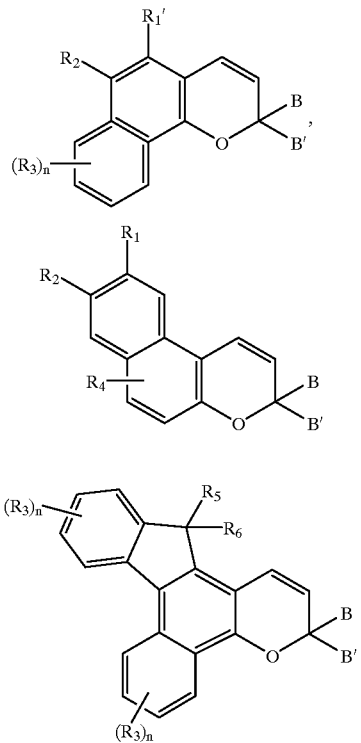

wherein, (a) $R_1$, $R_1'$, each $R_3$, $R_4$, $R_5$ or $R_6$ is the group R represented by the formula:

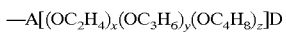

or

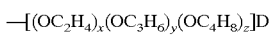

wherein —A— is —C(O)— or —CH$_2$—, D is a polymerizable group selected from hydroxy, (meth)acryloxy or epoxy, x, y and z are each a number between 0 and 50, and the sum of x, y and z is between 1 and 50; $R_2$ is the group R or mono R-substituted phenyl; provided that there is at least one R group or mono R-substituted phenyl on the naphtho or indeno portion of said naphthopyran; and provided further, that if $R_1$, $R_1'$, $R_3$, $R_4$, $R_5$ or $R_6$ is not the group R and $R_2$ is not the group R or mono R-substituted phenyl, then:

(b) $R_1$ is hydrogen, $C_1$–$C_3$ alkyl or the group, —C(O)W, W being —OR$_7$, —N(R$_8$)R$_9$, piperidino or morpholino, wherein $R_7$ is allyl, $C_1$–$C_6$ alkyl, phenyl, mono($C_1$–$C_6$) alkyl substituted phenyl, mono($C_1$–$C_6$)alkoxy substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$) alkyl or $C_1$–$C_6$ haloalkyl; $R_8$ and $R_9$ are each selected from the group consisting of $C_1$–$C_6$ alkyl, $C_5$–$C_7$ cycloalkyl, phenyl, mono-substituted phenyl and di-substituted phenyl, said phenyl substituents being $C_1$–$C_6$ alkyl or $C_1$–$C_6$ alkoxy, and said halo substituent being chloro or fluoro;

(c) $R_1'$ is $C_1$–$C_3$ alkyl or the group, —C(O)W, W being —OR$_7$, —N(R$_8$)R$_9$, piperidino or morpholino, wherein $R_7$ is allyl, $C_1$–$C_6$ alkyl, phenyl, mono($C_1$–$C_6$)alkyl substituted phenyl, mono($C_1$–$C_6$)alkoxy substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$) alkyl or $C_1$–$C_6$ haloalkyl; $R_8$ and $R_9$ are each selected from the group consisting of $c_1$–$C_6$ alkyl, $C_5$–$C_7$ cycloalkyl, phenyl, mono-substituted phenyl and di-substituted phenyl, said phenyl substituents being $C_1$–$C_6$ alkyl or $C_1$–$C_6$ alkoxy, and said halo substituent being chloro or fluoro;

(d) $R_2$, each $R_3$, and $R_4$ are selected from the group consisting of hydrogen, $C_1$–$C_6$ alkyl, $C_3$–$C_7$ cycloalkyl, phenyl, mono-substituted phenyl, di-substituted phenyl and the groups —OR$_{10}$ and —OC(O)R$_{10}$, wherein $R_{10}$ is $C_1$–$C_6$ alkyl, phenyl($C_1$–$C_3$)alkyl, mono($C_1$–$C_6$) alkyl substituted phenyl ($C_1$–$C_3$)alkyl, mono ($C_1$–$C_6$) alkoxy substituted phenyl($C_1$–$C_3$)alkyl, $C_1$–$C_6$ alkoxy ($C_2$–$C_4$)alkyl, $C_3$–$C_7$ cycloalkyl or mono($C_1$–$C_4$)alkyl substituted $C_3$–$C_7$ cycloalkyl, and n is selected from the integers 0, 1 and 2 and said phenyl substituent being $C_1$–$C_6$ alkyl or $C_1$–$C_6$ alkoxy;

(e) $R_5$ and $R_6$ together form an oxo group, a spiro-carbocyclic ring containing 3 to 6 carbon atoms or a spiro-heterocyclic group containing 1 or 2 oxygen atoms and 3 to 6 carbon atoms including the spirocarbon atom, said spiro-carbocyclic and spiro-heterocyclic groups being annellated with 0, 1 or 2 benzene rings; or $R_5$ and $R_6$ are each hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro, the group, —C(O)X, wherein X is hydroxy, $C_1$–$C_6$ alkyl, $C_1$–$C_6$ alkoxy, phenyl, mono-substituted phenyl, amino, mono($C_1$–$C_6$)alkylamino, or di($C_1$–$C_6$) alkylamino; or $R_5$ and $R_6$ are each the group, —OR$_{11}$, wherein $R_{11}$ is $C_1$–$C_6$ alkyl, phenyl($C_1$–$C_3$)alkyl, mono ($C_1$–$C_6$)alkyl substituted phenyl($C_1$–$C_3$)alkyl, mono ($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$) alkyl substituted $C_3$–$C_7$ cycloalkyl, $C_1$–$C_6$ chloroalkyl, $C_1$–$C_6$ fluoroalkyl, allyl, the group, —CH(R$_{12}$)Y, wherein $R_{12}$ is hydrogen or $C_1$–$C_3$ alkyl and Y is CN, CF$_3$, or COOR$_{13}$ and $R_{13}$ is hydrogen or $C_1$–$C_3$ alkyl; or $R_{11}$ is the group, —C(O)Z, wherein Z is hydrogen, $C_1$–$C_6$ alkyl, $C_1$–$C_6$ alkoxy, the unsubstituted, mono-or di-substituted aryl groups phenyl or naphthyl, phenoxy, mono- or di-($C_1$–$C_6$)alkyl substituted phenoxy, mono- or di-($C_1$–$C_6$)alkoxy substituted phenoxy, amino, mono ($C_1$–$C_6$)alkylamino, di($C_1$–$C_6$)alkylamino, phenylamino, mono- or di-($C_1$–$C_6$)alkyl substituted phenylamino, or mono- or di-($C_1$–$C_6$)alkoxy substituted phenylamino, each of said phenyl, benzyl and aryl group substituents being $C_1$–$C_6$ alkyl or $C_1$–$C_6$ alkoxy;

(f) B is a mono R-substituted phenyl; and (g) B' is selected from the group consisting of:
  (i) the unsubstituted, mono-, di- and tri-substituted aryl groups, phenyl and naphthyl;
  (ii) 9-julolidinyl and the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (g)(i) and (ii) being selected from the group consisting of hydroxy, aryl, mono($C_1$–$C_6$)alkoxyaryl, di($C_1$–$C_6$) alkoxyaryl, mono($C_1$–$C_6$)alkylaryl, di($C_1$–$C_6$) alkylaryl, chloroaryl, fluoroaryl, $C_3$–$C_7$ cycloalkylaryl, $C_3-C_7$ cycloalkyl, $C_3-C_7$ cycloalkyloxy, $C_3-C_7$ cycloalkyloxy($C_1-C_6$)alkyl, $C_3-C_7$ cycloalkyloxy($C_1-C_6$)alkoxy, aryl($C_1-C_6$) alkyl, aryl($C_1-C_6$)alkoxy, aryloxy, aryloxy($C_1-C_6$) alkyl, aryloxy($C_1-C_6$)alkoxy, mono- and di-($C_1-C_6$) alkylaryl($C_1-C_6$)alkyl, mono- and di-($C_1-C_6$) alkoxyaryl($C_1-C_6$)alkyl, mono- and di-($C_1-C_6$) alkylaryl($C_1-C_6$)alkoxy, mono- and di-($C_1-C_6$) alkoxyaryl($C_1-C_6$)alkoxy, amino, mono($C_1-C_6$) alkylamino, di($C_1-C_6$)alkylamino, diarylamino, N-($C_1-C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1-C_6$ alkyl, $C_1-C_6$ chloroalkyl, $C_1-C_6$ fluoroalkyl, $C_1-C_6$ alkoxy, mono ($C_1-C_6$)alkoxy($C_1-C_4$)alkyl, acryloxy, methacryloxy, bromo, chloro and fluoro, said aryl being phenyl or naphthyl;

(iii) the unsubstituted or mono-substituted groups, pyrazolyl, imidazolyl, pyridyl, pyrazolinyl, imidazolinyl, pyrrolinyl, phenothiazinyl, phenoxazinyl, phenazinyl or acridinyl, each of said substituents being selected from the group consisting of $C_1-C_6$ alkyl, $C_1-C_6$ alkoxy, phenyl, fluoro, chloro and bromo;

(iv) monosubstituted phenyl, having a substituent at the para position that is a linking group, —(CH$_2$)$_t$— or —O—(CH$_2$)$_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran;

(v) the groups represented by the following graphic formulae:

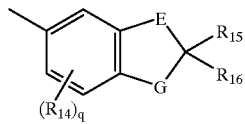 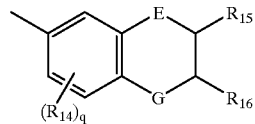

wherein E is carbon or oxygen and G is oxygen or substituted nitrogen, provided that when G is substituted nitrogen, E is carbon, said nitrogen substituents being selected from the group consisting of hydrogen, $C_1-C_6$ alkyl and $C_2-C_6$ acyl; each $R_{14}$ is $C_1-C_6$ alkyl, $C_1-C_6$ alkoxy, hydroxy, chloro or fluoro; $R_{15}$ and $R_{16}$ are each hydrogen or $C_1-C_6$ alkyl; and q is the integer 0, 1 or 2;

(vi) $C_1-C_6$ alkyl, $C_1-C_6$ chloroalkyl, $C_1-C_6$ fluoroalkyl, $C_1-C_6$ alkoxy($C_1-C_4$)alkyl, $C_3-C_6$ cycloalkyl, mono($C_1-C_6$)alkoxy($C_3-C_6$)cycloalkyl, mono($C_1-C_6$)alkyl($C_3-C_6$)-cycloalkyl, chloro ($C_3-C_6$)cycloalkyl, fluoro($C_3-C_6$)cycloalkyl and $C_4-C_{12}$ bicycloalkyl; and (vii) the group represented by the following graphic formula:

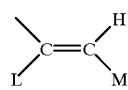

wherein L is hydrogen or $C_1-C_4$ alkyl and M is selected from the unsubstituted, mono-, and di-substituted members of the group consisting of naphthyl, phenyl, furanyl and thienyl, each of said group substituents being $C_1-C_4$ alkyl, $C_1-C_4$ alkoxy, fluoro or chloro.

2. A naphthopyran compound represented by the following graphic formulae:

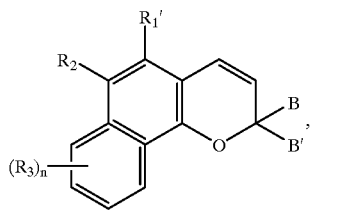

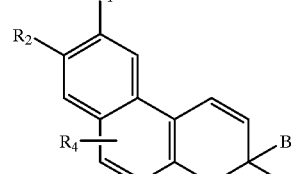

or

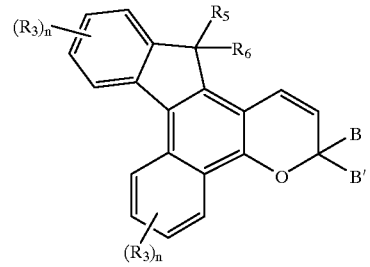

wherein, (a) $R_1$, $R_1'$, each $R_3$, $R_4$, $R_5$ or $R_6$ is the group R represented by the formula:

or

wherein —A— is —C(O)— or —CH$_2$—, D is a polymerizable group selected from hydroxy, (meth) acryloxy or epoxy; x, y and z are each a number between 0 and 50, and the sum of x, y and z is between 1 and 50; $R_2$ is the group R or a mono R-substituted phenyl; provided that there is at least one R group or mono R-substituted phenyl on said naphthopyran; and provided further, that if $R_1$, $R_1'$, $R_3$, $R_4$, $R_5$ or $R_6$ is not the group R and $R_2$ is not the group R or mono R-substituted phenyl, then:

(b) $R_1$ is hydrogen, $C_1-C_3$ alkyl or the group, —C(O)W, W being —OR$_7$, —N(R$_8$)R$_9$, piperidino or morpholino, wherein $R_7$ is allyl, $C_1-C_6$ alkyl, phenyl, mono($C_1-C_6$) alkyl substituted phenyl, mono($C_1-C_6$)alkoxy substituted phenyl, phenyl($C_1-C_3$)alkyl, mono($C_1-C_6$)alkyl substituted phenyl($C_1-C_3$)alkyl, mono($C_1-C_6$)alkoxy substituted phenyl($C_1-C_3$)alkyl, $C_1-C_6$ alkoxy($C_2-C_4$) alkyl or $C_1-C_6$ haloalkyl; $R_8$ and $R_9$ are each selected from the group consisting of $C_1-C_6$ alkyl, $C_5-C_7$ cycloalkyl, phenyl, mono-substituted phenyl and di-substituted phenyl, said phenyl substituents being $C_1-C_6$ alkyl or $C_1-C_6$ alkoxy, and said halo substituent being chloro or fluoro;

(c) $R_1'$ is $C_1$–$C_3$ alkyl or the group, —C(O)W, W being —$OR_7$, —N($R_8$)$R_9$, piperidino or morpholino, wherein $R_7$ is allyl, $C_1$–$C_6$ alkyl, phenyl, mono($C_1$–$C_6$)alkyl substituted phenyl, mono($C_1$–$C_6$)alkoxy substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl or $C_1$–$C_6$ haloalkyl; $R_8$ and $R_9$ are each selected from the group consisting of $C_1$–$C_6$ alkyl, $C_5$–$C_7$ cycloalkyl, phenyl, mono-substituted phenyl and di-substituted phenyl, said phenyl substituents being $C_1$–$C_6$ alkyl or $C_1$–$C_6$ alkoxy, and said halo substituent being chloro or fluoro;

(d) $R_2$, each $R_3$, and $R_4$ are selected from the group consisting of hydrogen, $C_1$–$C_6$ alkyl, $C_3$–$C_7$ cycloalkyl, phenyl, mono-substituted phenyl, di-substituted phenyl and the groups —$OR_{10}$ and —OC(O)$R_{10}$, wherein $R_{10}$ is $C_1$–$C_6$ alkyl, phenyl($C_1$–$C_3$)alkyl, mono($C_1$–$C_6$) alkyl substituted phenyl($C_1$–$C_3$)alkyl, mono($C_1$–$C_6$) alkoxy substituted phenyl($C_1$–$C_3$)alkyl, $C_1$–$C_6$ alkoxy ($C_2$–$C_4$)alkyl, $C_3$–$C_7$ cycloalkyl or mono($C_1$–$C_4$)alkyl substituted $C_3$–$C_7$ cycloalkyl, and n is selected from the integers 0, 1 and 2 and said phenyl substituent being $C_1$–$C_6$ alkyl or $C_1$–$C_6$ alkoxy;

(e) $R_5$ and $R_6$ together form an oxo group, a spiro-carbocyclic ring containing 3 to 6 carbon atoms or a spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings; or $R_5$ and $R_6$ are each hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro, the group, —C(O)X, wherein X is hydroxy, $C_1$–$C_6$ alkyl, $C_1$–$C_6$ alkoxy, phenyl, mono-substituted phenyl, amino, mono($C_1$–$C_6$)alkylamino, or di($C_1$–$C_6$)alkylamino, or $R_5$ and $R_6$ are each the group, —$OR_{11}$, wherein $R_{11}$ is $C_1$–$C_6$ alkyl, phenyl($C_1$–$C_3$) alkyl, mono($C_1$–$C_6$)alkyl substituted phenyl($C_1$–$C_3$) alkyl, mono($C_1$–$C_6$)alkoxy substituted phenyl($C_1$–$C_3$) alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, the group, —CH($R_{12}$)Y, wherein $R_{12}$ is hydrogen or $C_1$–$C_3$ alkyl and Y is CN, $CF_3$, or COO$R_{13}$ and $R_{13}$ is hydrogen or $C_1$–$C_3$ alkyl, or $R_{11}$ is the group, —C(O)Z, wherein Z is hydrogen, $C_1$–$C_6$ alkyl, $C_1$–$C_6$ alkoxy, the unsubstituted, mono-or di-substituted aryl groups phenyl or naphthyl, phenoxy, mono- or di-($C_1$–$C_6$)alkyl substituted phenoxy, mono-or di-($C_1$–$C_6$)alkoxy substituted phenoxy, amino, mono($C_1$–$C_6$)alkylamino, di($C_1$–$C_6$)alkylamino, phenylamino, mono- or di-($C_1$–$C_6$)alkyl substituted phenylamino, or mono- or di-($C_1$–$C_6$)alkoxy substituted phenylamino, each of said phenyl, benzyl and aryl group substituents being $C_1$–$C_6$ alkyl or $C_1$–$C_6$ alkoxy; and (f) B and B' are each selected from the group consisting of
   (i) mono R-substituted phenyl;
   (ii) the unsubstituted, mono-, di- and tri-substituted aryl groups, phenyl and naphthyl;
   (iii) 9-julolidinyl and the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (f)(ii) and (iii) being selected from the group consisting of hydroxy, aryl, mono($C_1$–$C_6$)alkoxyaryl, di($C_1$–$C_6$) alkoxyaryl, mono($C_1$–$C_6$)alkylaryl, di($C_1$–$C_6$) alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$) alkyl, aryl($C_1$–$C_6$)alkoxy, aryloxy, aryloxy($C_1$–$C_6$) alkyl, aryloxy($C_1$–$C_6$)alkoxy, mono- and di-($C_1$–$C_6$) alkylaryl($C_1$–$C_6$)alkyl, mono- and di-($C_1$–$C_6$) alkoxyaryl($C_1$–$C_6$)alkyl, mono- and di-($C_1$–$C_6$) alkylaryl($C_1$–$C_6$)alkoxy, mono- and di-($C_1$–$C_6$) alkoxyaryl($C_1$–$C_6$)alkoxy, amino, mono($C_1$–$C_6$) alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, acryloxy, methacryloxy, bromo, chloro and fluoro, said aryl being phenyl or naphthyl;
   (iv) the unsubstituted or mono-substituted groups, pyrazolyl, imidazolyl, pyridyl, pyrazolinyl, imidazolinyl, pyrrolinyl, phenothiazinyl, phenoxazinyl, phenazinyl or acridinyl, each of said substituents being selected from the group consisting of $C_1$–$C_6$ alkyl, $C_1$–$C_4$ alkoxy, phenyl, fluoro, chloro and bromo;
   (v) monosubstituted phenyl, having a substituent at the para position that is a linking group, —($CH_2$)$_t$— or —O—($CH_2$)$_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran;
   (vi) the groups represented by the following graphic formulae:

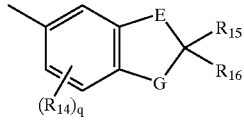 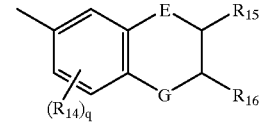

wherein E is carbon or oxygen and G is oxygen or substituted nitrogen, provided that when G is substituted nitrogen, E is carbon, said nitrogen substituents being selected from the group consisting of hydrogen, $C_1$–$C_6$ alkyl and $C_2$–$C_6$ acyl; each $R_{14}$ is $C_1$–$C_6$ alkyl, $C_1$–$C_6$ alkoxy, hydroxy, chloro or fluoro; $R_{15}$ and $R_{16}$ are each hydrogen or $C_1$–$C_6$ alkyl; and q is the integer 0, 1 or 2;
   (v) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono ($C_1$–$C_6$)alkoxy($C_3$–$C_6$)cycloalkyl, mono($C_1$–$C_6$) alkyl($C_3$–$C_6$)-cycloalkyl, chloro($C_3$–$C_6$)cycloalkyl, fluoro($C_3$–$C_6$)cycloalkyl and $C_4$–$C_{12}$ bicycloalkyl; and
   (vi) the group represented by the following graphic formula:

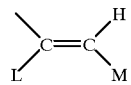

wherein L is hydrogen or $C_1$–$C_4$ alkyl and M is selected from the unsubstituted, mono-, and di-substituted members of the group consisting of naphthyl, phenyl, furanyl and thienyl, each of said group substituents being $C_1$–$C_4$ alkyl, $C_1$–$C_4$ alkoxy, fluoro or chloro; or (g) B and B' taken together form fluoren-9-ylidene, mono-, or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.

3. The naphthopyran of claim 2 wherein there is one R group or mono R-substituted phenyl on said naphthopyran.

4. The naphthopyran of claim 2 wherein
(a) —A is —C(O)—, D is hydroxy or (meth)acryloxy; x and y are each a number between 0 and 50, z is 0 and the sum of x and y is between 1 and 50;
(b) $R_1$ or $R_1'$ is the group, —C(O)W, W being —$OR_7$ or —N($R_8$)$R_9$, wherein $R_7$ is $C_1$–$C_4$ alkyl, phenyl, mono ($C_2$–$C_4$)alkyl substituted phenyl, mono($C_1$–$C_4$)alkoxy substituted phenyl, phenyl($C_1$–$C_2$)alkyl, mono($C_1$–$C_4$) alkyl substituted phenyl($C_1$–$C_2$)alkyl, mono($C_1$–$C_4$) alkoxy substituted phenyl($C_1$–$C_2$)alkyl, mono($C_1$–$C_4$) alkoxy($C_2$–$C_3$)alkyl or $C_1$–$C_4$ haloalkyl; $R_8$ and $R_9$ are each selected from the group consisting of $C_1$–$C_4$ alkyl, $C_5$–$C_7$ cycloalkyl, phenyl, mono-substituted phenyl and di-substituted phenyl, said phenyl substituents being $C_1$–$C_4$ alkyl or $C_1$–$C_4$ alkoxy, said halo substituents being chloro or fluoro;
(c) $R_2$, each $R_3$, and $R_4$ are selected from the group consisting of hydrogen, $C_1$–$C_3$ alkyl, $C_3$–$C_5$ cycloalkyl, phenyl, mono-substituted phenyl, di-substituted phenyl and the group —$OR_{10}$, wherein $R_{10}$ is $C_1$–$C_4$ alkyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, $C_1$–$C_4$ alkoxy($C_2$–$C_4$)alkyl, $C_5$–$C_7$ cycloalkyl or mono($C_1$–$C_3$)alkyl substituted $C_5$–$C_7$ cycloalkyl and said phenyl substituents being $C_1$–$C_3$ alkyl or $C_1$–$C_3$ alkoxy;
(d) $R_5$ and $R_6$ are each selected from the group consisting of hydrogen, hydroxy, $C_1$–$C_4$ alkyl, $C_3$–$C_6$ cycloalkyl, chloro, fluoro and the group, —$R_{11}$, wherein $R_{11}$ is $C_1$–$C_3$ alkyl, phenyl($C_1$–$C_2$)alkyl, mono($C_1$–$C_3$)alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$) alkyl, $C_1$–$C_3$ chloroalkyl, $C_1$–$C_3$ fluoroalkyl, the group, —CH($R_{12}$)Y, wherein $R_{12}$ is hydrogen or $C_1$–$C_2$ alkyl and Y is CN or COO$R_{13}$, and $R_{13}$ is hydrogen or $C_1$–$C_2$ alkyl, or $R_{11}$ is the group, —C(O)Z, wherein Z is hydrogen, $C_1$–$C_3$ alkyl, $C_1$–$C_3$ alkoxy, phenyl, naphthyl, mono-substituted aryl groups, phenyl or naphthyl, phenoxy, mono- or di-($C_1$–$C_3$)alkyl substituted phenoxy, mono- or di-($C_1$–$C_3$)alkoxy substituted phenoxy, mono($C_1$–$C_3$)alkylamino, phenylamino, mono- or di-($C_1$–$C_3$)alkyl substituted phenylamino, or mono- or di-($C_1$–$C_3$)alkoxy substituted phenylamino, and said aryl substituents being $C_1$–$C_3$ alkyl or $C_1$–$C_3$ alkoxy;

(e) B and B' are each selected from the group consisting of:
(i) mono R-substituted phenyl;
(ii) phenyl, mono-substituted and di-substituted phenyl;
(iii) the unsubstituted, mono- and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in (e) (ii) and (iii) being selected from the group consisting of hydroxy, aryl, arlyoxy, aryl($C_1$–$C_3$)alkyl, amino, mono($C_1$–$C_3$) alkylamino, di($C_1$–$C_3$)alkylamino, N-($C_1$–$C_3$) alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy ($C_1$–$C_3$)alkyl, chloro and fluoro;
(iv) the groups represented by the following graphic formulae:

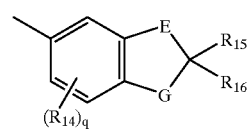 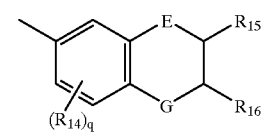

wherein E is carbon and G is oxygen, $R_{14}$ is $C_1$–$C_3$ alkyl or $C_1$–$C_3$ alkoxy; $R_{15}$ and $R_{16}$ are each hydrogen or $C_1$–$C_4$ alkyl; and q is 0 or 1;
(v) $C_1$–$C_4$ alkyl; and
(vi) the group represented by the following graphic formula:

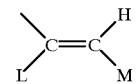

wherein L is hydrogen or methyl and M is phenyl or mono-substituted phenyl, said phenyl substituents being $C_1$–$C_3$ alkyl, $C_1$–$C_3$ alkoxy or fluoro; or
(f) B and B' taken together form fluoren-9-ylidene, mono-substituted fluoren-9-ylidene or a member selected from the group consisting of saturated $C_3$–$C_8$ spiromonocyclic hydrocarbon rings, saturated $C_7$–$C_{10}$ spirobicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

5. The naphthopyran of claim 4 wherein:
(a) —A is —C(O)— and D is hydroxy; x is a number between 1 and 50, y and z are each 0;
(b) $R_1$ or $R_1'$ is the group, —C(O)W, wherein W is the group, —$OR_7$, and $R_7$ is $C_1$–$C_3$ alkyl;
(c) $R_2$, each $R_3$, and $R_4$ are selected from the group consisting of hydrogen, $C_1$–$C_3$ alkyl, phenyl, mono-substituted phenyl, di-substituted phenyl and the group, $OR_{10}$, wherein $R_{10}$ is $C_1$–$C_3$ alkyl and said phenyl substituents being ethyl or methoxy;
(d) $R_5$ and $R_6$ are each hydrogen, hydroxy, $C_1$–$C_4$ alkyl, or the group, —$OR_{11}$, wherein $R_{11}$ is $C_1$–$C_3$ alkyl;
(e) B and B' are each consisting of:
(i) mono R-substituted phenyl;
(ii) phenyl, mono- and di-substituted phenyl;
(iii) the unsubstituted, mono- and di-substituted heteroaromatic groups furanyl, benzofuran-2-yl, thienyl and benzothien-2-yl, each of said phenyl and heteroaromatic substituents in (e) (ii) and (iii) being selected from the group consisting of hydroxy, $C_1$–$C_3$ alkyl, $C_1$–$C_3$ alkoxy, phenyl, indolino, fluoro and chloro; and (iv) the group represented by the following graphic formula:

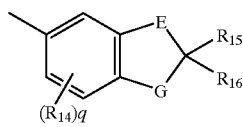

wherein E is carbon and G is oxygen, $R_{14}$ is $C_1$–$C_3$ alkyl or $C_1$–$C_3$ alkoxy; $R_{15}$ and $R_{16}$ are each hydrogen or $C_1$–$C_3$ alkyl; and q is 0 or 1; or (f) B and B' taken together form fluoren-9-ylidene, adamantylidene, bornylidene, norbornylidene, or bicyclo[3.3.1]nonan-9-ylidene.

6. A naphthopyran compound selected from the group consisting of:

(a) 2,2-bis(4-methoxyphenyl)-5-(2-hydroxyethoxycarbonyl)-6-phenyl-[2H]-naphtho[1,2-b]pyran;

(b) 2,2-bis(4-methoxyphenyl)-5-(2-(2-hydroxyethoxy)ethoxycarbonyl)-6-phenyl-[2H]-naphtho[1,2-b]pyran;

(c) 2,2-bis(4-methoxyphenyl)-5-(2-(2-(2-hydroxyethoxy)ethoxy)ethoxycarbonyl)-6-phenyl-[2H]naphtho[1,2-b]pyran;

(d) 2,2-bis(4-methoxyphenyl)-5-(2-(2-(2-hydroxyethoxy)ethoxy)ethoxy)ethoxycarbonyl)-6-phenyl-[2H]-naphtho[1,2-b]pyran;

(e) 2,2-bis(4-methoxyphenyl)-5-methoxycarbonyl-6-(2-hydroxyethoxy)ethoxy-[2H]-naphtho[1,2-b]pyran;

(f) 2-(4-(2-(2-hydroxyethoxy)ethoxy)ethoxyphenyl)-2-phenyl-5-methoxycarbonyl-6-methyl-9-methoxy-[2H]-naphtho[1,2-b]pyran;

(g) 2,2-bis(4-methoxyphenyl)-5-methoxycarbonyl-6-phenyl-9-(2-hydroxyethoxy)-[2H]-naphtho[1,2-b]pyran; and (h) 2,2-bis(4-methoxyphenyl)-5-methoxycarbonyl-6-(4-(2-hydroxyethoxy)phenyl)-[2H]-naphtho[1,2-b]pyran.

(i) 2-phenyl-2-(4-(2-(2-methylprop-2-enoyloxy)ethoxy)phenyl)-5-(methoxycarbonyl)-6-(2-(2-methylprop-2-enoxyloxy)ethoxy)-[2H]-naphtho[1,2-b]pyran;

(j) 2,2,6-triphenyl-5-(2-(2-(2-(2-methylprop-2-enoxyloxy)ethoxy)ethoxy)ethoxycarbonyl)-[2H]-naphtho[1,2-b]pyran;

(k) 2,2,6-triphenyl-5-(2-(2-(2-(oxiran-2-ylmethoxy)ethoxy)ethoxy)ethoxycarbonyl)-[2H]-naphtho[1,2-b]pyran;

(l) 3,3-di(4-methoxyphenyl)-6,11,13-trimethyl-13-(2-(2-hydroxyethoxy)ethoxy)-indeno[2,1-f]naphtho[1,2-b]pyran;

(m) 3,3-di(4-methoxyphenyl)-6,11,13-trimethyl-13-(2-(2-(2-hydroxyethoxy)ethoxy)ethoxy)ethoxy)-indeno[2,1-f]naphtho[1,2-b]pyran;

(n) 3,3-bis(4-methoxyphenyl)-9-methoxycarbonyl-8-(2-hydroxyethoxy)ethoxy-[3H]-naphtho[2,1-b]pyran; and (o) 3-(4-(2-(2-hydroxyethyl)ethoxy)ethoxyphenyl)-3-phenyl-9-methoxycarbonyl-8-methoxy-[3H]-naphtho[2,1-b]pyran.

7. A photochromic article comprising a polymeric organic host material selected from the group consisting of poly (methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 5.

8. A photochromic article comprising a polymeric organic host material and a photochromic amount of the naphthopyran compound of claim 1.

9. The photochromic article of claim 8 wherein the polymeric organic host material is selected from the group consisting of polyacrylates, polymethacrylates, poly ($C_1$–$C_{12}$) alkyl methacrylates, polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

10. The photochromic article of claim 9 wherein the polymeric organic material is a homopolymer or copolymer of monomer(s) selected from the group consisting of acrylates, methacrylates, methyl methacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethylol propane triacrylate.

11. The photochromic article of claim 8 wherein the photochromic compound is present in an amount of from 0.05 to 1.0 milligram per square centimeter of polymeric organic host material surface to which the photochromic substance(s) is incorporated or applied.

12. The photochromic article of claim 8 wherein said polymeric organic host material is an optical element.

13. The photochromic article of claim 12 wherein said optical element is a lens.

14. A photochromic article comprising, in combination, a solid substrate and a photochromic amount of each of (a) at least one naphthopyran compound of claim 1, and (b) at least one other organic photochromic compound having at least one activated absorption maxima within the range of between 400 and 700 nanometers.

15. A photochromic article comprising a polymerizate of an optical organic resin monomer and a photochromic amount of the naphthopyran compound of claim 1.

16. The photochromic article of claim 15 wherein the refractive index of the polymerizate is from about 1.48 to about 1.75.

17. The photochromic article of claim 15 wherein the polymerizate is an optical element.

18. The photochromic article of claim 17 wherein said optical element is an ophthalmic lens or a contact lens.

19. A photochromic article comprising, in combination, a solid substrate and on at least one surface thereof a cured coating of a coating composition having a photochromic amount of the naphthopyran compound of claim 1.

20. The photochromic article of claim 19 wherein said coating composition is selected from the group consisting of a polymeric coating composition, paint and ink.

21. The photochromic article of claim 19 wherein the substrate is selected from the group consisting of glass, masonry, textiles, ceramics, metals, wood, paper and polymeric organic material.

* * * * *